US007381426B2

(12) United States Patent
Vail

(10) Patent No.: US 7,381,426 B2
(45) Date of Patent: Jun. 3, 2008

(54) TARGETED DELIVERY OF BIOACTIVE FACTORS TO THE SYSTEMIC SKELETON

(75) Inventor: Neal K. Vail, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 722 days.

(21) Appl. No.: 10/350,805

(22) Filed: Jan. 24, 2003

(65) Prior Publication Data

US 2003/0203038 A1  Oct. 30, 2003

Related U.S. Application Data

(60) Provisional application No. 60/351,714, filed on Jan. 24, 2002.

(51) Int. Cl.
*A61K 9/14* (2006.01)

(52) U.S. Cl. .................. 424/489; 514/772; 977/773

(58) Field of Classification Search .................. None
See application file for complete search history.

(56) References Cited

U.S. PATENT DOCUMENTS

| 4,942,036 A | 7/1990 | Geho et al. | |
|---|---|---|---|
| 5,013,649 A | 5/1991 | Wang et al. | 435/69.1 |
| 5,270,300 A * | 12/1993 | Hunziker | 514/12 |
| 5,401,511 A | 3/1995 | Margalit | 424/450 |
| 5,603,872 A | 2/1997 | Margalit | 264/4.3 |
| 5,648,056 A | 7/1997 | Tanaka | 423/445 |
| 5,853,746 A * | 12/1998 | Hunziker | 424/426 |
| 5,876,747 A | 3/1999 | Stracher et al. | |
| 5,889,155 A | 3/1999 | Ashkenazi et al. | 530/351 |
| 5,998,369 A | 12/1999 | Khosla et al. | |
| 6,045,821 A * | 4/2000 | Garrity et al. | 424/450 |
| 2002/0034474 A1 | 3/2002 | Sabel et al. | |
| 2003/0203038 A1 | 10/2003 | Vail | |

FOREIGN PATENT DOCUMENTS

| WO | 0137883 | 5/2001 |
|---|---|---|
| WO | 2004089345 | 10/2004 |

OTHER PUBLICATIONS

Allen et al., "Therapeutic opportunities for targeted liposomal drug delivery," *Advanced Drug Delivery Reviews*, 21:117-133, 1996.
Bikle et al., "Alendronate increased skeletal mass of growing rats during unloading by inhibiting resorption of calcified cartilage," *J. Bone Miner. Res.*, 9:1777-1787, 1994.

(Continued)

*Primary Examiner*—Michael G. Hartley
*Assistant Examiner*—Eric E Silverman
(74) *Attorney, Agent, or Firm*—Grossman, Tucker et al.

(57) ABSTRACT

The invention provides methods and compositions for the delivery of bioactive factors to the systemic skeleton. The methods of the invention allow targeted delivery of bioactive factors to bone using nanocapsules. Timed release of bioactive factors may also be used to increase the efficacy of treatment. The methods of the invention have wide applicability for the treatment or prevention of bone-associated maladies.

70 Claims, 5 Drawing Sheets

OTHER PUBLICATIONS

Bikle et al., "Skeletal unloading induces resistance to insulin-like growth factor I," *J. Bone Miner. Res.*, 9:1789-1796, 1994.

Carmeliet et al., "Gene expression related to the differentiation of osteoblastic cells is altered by microgravity," *Bone*, 22:139S-143S, 1998.

Centrella, et al. "Transforming growth factor β is a bifunctional regulator of replication and collagen synthesis in osteoblast-enriched cell cultures from fetal rat bone," *J. Biol. Chem.*, 262:2869-2874, 1987.

Chenu, et al., "Transforming growth factor β inhibits formation of osteoclast-like cells in long-term human marrow cultures," *Proc. Natl. Acad. Sci. USA*, 85:5683-5687, 1988.

Cronhjort et al., "Sympathotropic drugs and the distribution of $^{99m}$Tc-hydroxymethylene disphosphonate," *Acta Radiol.*, 40:309-313, 1999.

Davis and Jones, "Comparison of $^{99m}$Tc-labeled phosphate and phosphonate agents for skeletal imaging," *Semin. Nucl. Med.*, 6:19-31, 1976.

Fleiner et al., "Studies on protein—liposome coupling using novel thiol-reactive coupling lipids: influence of spacer length and polarity," *Bioconjugate Chem.*, 12:470-475, 2001.

Forssen and Willis, "Ligand-targeted liposomes," *Adv. Drug Delivery Reviews*, 29:249-271, 1998.

Fujisaki et al., "Osteotropic drug delivery system (ODDS) based on bisphosphonic prodrug. I: Synthesis and in vivo characterization of osteotropic carboxyfluorescein," *J. Drug Targeting*, 3:273-282, 1995.

Fujisaki et al., "Osteotropic drug delivery system (ODDS) based on biosphosphonic prodrug. IV effectos of osteotropic estradiol bon bone mineral density and uterine weight in ovariectomized rats," *J. Drug. Targeting*, 5:129-138, 1997.

Fujisaki et al., "Physicochemical characterization of bisphosphonic carboxyfluorescein for osteotropic drug delivery," *J. Pharm. Pharmacol.*, 48:798-800, 1996.

Gao et al., "Diacyllipid-polymer micelles as nanocarriers for poorly soluble anticancer drugs," *Nano Letters*, 2:979-982, 2002.

Holick, "Microgravity-induced bone loss—will it limit human space exploration?" *The Lancet*, 355:1569-1570, 2000.

Ishida et al., "A combinatorial approach to producing sterically stabilized (Stealth) immunoliposomal drugs," *FEBS Letters*, 460:129-133, 1999.

Jeppesen et al., "Impact of polymer tether length on multiple ligand-receptor bond formation," *Science*, 293:465-468, 2001.

Kamps et al., "Massive targeting of liposomes, surface-modified with anionized albumins, to hepatic endothelial cells," *Proc. Natl. Acad. Sci., USA*, 94:11681-11685, 1997.

Kantoci et al., "Synthesis of aminobisphosphonate," *Synth. Comm.*, 26:2037-2043, 1996.

Kasugai et al., "Selective drug delivery system to bone: small peptide (Asp)$_6$ conjugation," *J. Bone and Mineral Research*, 15:936-943, 2000.

Lantto et al., "$^{99m}$Tc-MDP and $^{99m}$Tc-DPD in pathologic bone lesions. A visual and quantitative comparision," *Acta Radiol.*, 28:631-633, 1987.

Lee and Low, "Folate-mediated tumor cell targeting of lipsome-entrapped doxorubicin in vitro," *Biochim. Biophys. Acta*, 1233:134-144, 1995.

Machwate et al., "Systemic administration of transforming growth factor-β2 prevents the impaired bone formation and osteopenia induced by unloading in rats," *J. Clin. Invest.*, 96:1245-1253, 1995.

McCarthy et al., "Investigation of bone changes in microgravity during long and short duration space flight: comparison of techniques," *Eur. J. Clin. Invest.*, 30:1044-1054, 2000.

Moreira et al., "Use of the post-insertion technique to insert peptide ligands into pre-formed stealth liposomes with retention of binding activity and cytotoxicity," *Pharmaceutical Research*, 19:265-269, 2002.

Mundy, "Bone-Resorbing cells," In: *Primer on the metabolic bone diseases and disorders of mineral metabolism*, Favus, (Ed.) Amer. Soc. of Bone and Mineral Research, Chapter 3:16-24, 1996.

Mundy, "Pathogenesis of osteoporosis and challenges for drug delivery," *Adv. Drug Delivery Rev.*, 42:165-173, 2000.

Nagata et al., "Biosynthesis of bone proteins [SPP-1 (secreted phosphoprotein-1, osteopontin), BSP (bone sialoprotein) and SPARC (osteonectin)] in association with mineralized-tissue formation by fetal-rat calvarial cells in culture," *Biochem. J.*, 274(Pt. 2):513-520, 1991.

Parfitt et al., "A new model for the regulation of bone resorption, with particular reference to the effects of bisphosphonates," *J. Bone Miner. Res.*, 11:150-159, 1996.

Rho et al., "Mechanical properties and the hierarchical structure of bone," *Medical Engineering and Physics*, 20:92-102, 1998.

ten Dijke and Iwata, "Growth factors for wound healing," *Bio/Technology*, 7:793-798, 1989.

Thérien and Shahum, "Immunopotentiation of the humoral response by liposomes: effect of a T cell polyclonal activator," *Cell. Immun.*, 116:320-330, 1988.

Uludag et al., "Bisphosphonate conjugation to proteins as a means to impart bone affinity," *Biotechnol. Prog.*, 16:258-267, 2000.

Uludag et al., "Bone affinity of a bisphosphonate-conjugated protein in vivo," *Biotechnol. Prog.*, 16:1115-1118, 2000.

Uster, et al., "Insertion of poly(ethylene glycol) derivatized phospholipid into pre-formed liposomes results in prolonged in vivo circulation time," *FEBS Letters*, 386:243-246, 1996.

Van Slooten et al., "Liposomes as sustained release system for human interferon-γ: biopharmaceutical aspects," *Biochim. Biophys. Acta*, 1530:134-145, 2001.

Vico et al., "Effects of long-term microgravity exposure on canellous and cortical weight-bearing bones of cosmonauts," *The Lancet*, 355:1607-1611, 2000.

Weissig et al., "Accumulation of protein-loaded long-circulating micelles and liposomes in subcutaneous Lewis lung carcinoma in mice," *Pharmaceutical Research*, 15:1552-1556, 1998.

Westerlind and Turner, "The skeletal effects of spaceflight in growing rats: tissue-specific alterations in mRNA levels for TGF-β," *J. Bone Miner. Res.*, 10:843-848, 1995.

Wu et al., "Increased microvascular permeability contributes to preferential accumulation of stealth liposomes in tumor tissue," *Cancer Res.*, 53:3765-3770, 1993.

Yokogawa et al., "Selective delivery of estradiol to bone by aspartic acid oligopeptide and its effects on ovariectomized mice," *Endocrinology*, 142(3):1228-1233, 2000.

U.S. Appl. No. 60/351,701, filed Jan. 24, 2002.

Allen et al., "Liposomes containing synthetic lipid derivatives of poly(ethylene glycol) show prolonged circulation half-lives in vivo," Biochim Biophys Acta, 1066:29-36, 1991.

Fleisch, Biophosphonates in Bone Disease, 2nd Ed., Patheon, NY, 1995.

Garrett et al., "Selective inhibitors of the osteoblast proteasome stimulate bone formation in vivo and in vitro," J. Clin Invest, 111:1771-1782, 2003.

Kyle et al., "Review of 1027 patients with newly diagnosed multiple myeloma," Mayo Clin Proc, 78:21-33, 2003.

Mayer et al., "Vesicles of variable sizes produced by a rapid extrusion procedure," Biochem Biophys Acta, 858:161-168, 1986.

Torchilin et al., "Structure and design of polymeric surfactant-based drug delivery systems," Journal of Controlled Release, 73(2-3_:137-172, 2001.

* cited by examiner

MBP            PEGylated Phospholipid

Scheme 1 - Thiolated Methylene Bisphosphonate

Amino-MBP     2-IT     TBP

Scheme 2 - Conjugation of Methylene Bisphosphonate to Functionalized Phospholipid TBP     DSPE-PEG-M     MBP-Lipid

TARGETED DELIVERY OF BIOACTIVE FACTORS TO THE SYSTEMIC SKELETON

The present application claims priority to U.S. provisional patent application, Ser. No. 60/351,714, filed Jan. 24, 2002. The entire contents of the above referenced disclosure is incorporated herein by reference and without disclaimer.

BACKGROUND OF THE INVENTION

1. Field of the Invention

The present invention relates generally to the field of medicine. More particularly, it concerns methods for delivering bioactive factors to bone.

2. Description of Related Art

Numerous pathological conditions are associated with abnormal bone cell function including osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), and age-related loss of bone mass. Loss of bone mass in particular can lead to skeletal failure such that bone fractures can result from the minimal trauma of everyday life. Such fractures cause significant illness, or morbidity, inasmuch as there is insufficient repair or healing of the fractures.

Osteoporosis is the most common cause of bone loss and is a leading cause of disability in the elderly, particularly in elderly women. Osteoporosis is a progressive disease which results in the reduction of total bone mass and increased bone fragility. This often results in spontaneous fractures of load-bearing bones and the physical and mental deterioration characteristic of immobilizing injuries. The most widely accepted preventive agent for osteoporosis currently in use is estrogen therapy. However, systemic administration of estrogen is not a viable option in women at elevated risk for breast or endometrial cancers (estrogen dependent tumors) or for men (Cooper, 1994). In addition, recent studies have shown that estrogen replacement therapies (ERT's) have other deleterious side-effects, calling into question the long-term effects of these therapies.

Bisphosphonates have been effective inhibitors of osteoclastic bone resorption and have been used to advantage in treating osteoporosis (Parfitt el al., 1996). Bisphosphonates have been shown to increase trabecular bone volume and inhibit the decrease in cancellous bone mass in hindlimb unloaded rats compared to treated controls. However, the amount of cartilage in trabecular bone in these animals significantly increases, indicating that the modeling process is altered and mineralized cartilage fails to be resorbed and replaced by bone.

Vitamin D (1,25D), calcium and thiazide diuretics have also been used alone or in combination to prevent bone loss associated with corticosteroid treatment. The goal of such therapy is to improve calcium absorption and decrease urinary excretion of calcium thus, reversing secondary hyperparathyroidism (Joseph, 1994). Calcium supplements are widely used in managing established osteoporosis but there have been few satisfactory prospective studies of calcium supplementation on bone density or on the risk of future fractures (Cooper, 1994).

Bone damage, such as bone fractures, represents another common bone malady. Although repair, healing and augmentation of bone require a complex series of events that are not well defined, it is known that specific, naturally occurring factors are required to achieve these objectives. Such factors are released or migrate into the injured areas, and stimulate osteoblasts, chondrocytes, and odontoblasts in bone and cartilage to stimulate matrix formation and remodeling of the wounded area (ten Dijke et al., 1989).

New bone can be formed by three basic mechanisms: osteogenesis, osteoconduction and osteoinduction. Cancellous bone and marrow grafts provide viable cells for such processes. Transforming growth factor-beta (TGF-β) has been shown to stimulate proliferation and matrix synthesis of osteoblastic cells (Centrella et al., 1987) and to inhibit the formation and activity of osteoclastic cells (Chenu et al. 1988). Members of the bone morphogenetic protein family have been shown to be useful for induction of cartilage and bone formation. For example, BMP-2 has been shown to be able to induce the formation of new cartilage and/or bone tissue (U.S. Pat. No. 5,013,649).

Weightlessness during spaceflight has also been a cause of bone loss. Countermeasures for such bone loss have been of the skeletal stress type, such as cycling, simulated running, and rowing (Baldwin el al., 1996). Studies show that exercise-induced skeletal stress serves to maintain and increase osteoblastic activity. However, these methods alone are insufficient to prevent bone volume losses, primarily because it is not possible to generate forces of equal magnitude to those encountered on Earth (McCarthy et al., 2000; Baldwin et al., 1996). Electrical stimulation of selected muscle groups in hindlimb unloaded rats also increases osteoblast activity and osteoid surfaces, but does not prevent decrease in trabecular bone volume or metaphyseal apposition rate (Zerath et al., 1995). Bisphosphonates such as alendronate minimize bone loss during unloading by inhibiting osteoclastic bone resorption, but do not prevent the unloading-induced suppression of bone formation (Bikle et al., 1994). Thus, antiresorbing agents are not ideal countermeasures to bone loss when the primary defect is reduced bone formation (McCarthy et al, 2000).

Growth hormone (GH) treatment of hypophysectomized rats has been shown to increase bone mass independent of whether the animals are loaded or unloaded. However, unloaded animals still show lower bone mass relative to treated animals for the same treatment protocol. Pharmacological doses of GH of 500 μg/ml also failed to mediate skeletal defects in hypophysectomized rats in response to hindlimb unloading, including decreased trabecular bone volume and cortical bone apposition rate (Halloran et al., 1995). Although systemic factors such as GH and 1,25D may modulate the response of bone to unloading, factors that locally regulate bone growth may have greater utility as countermeasure molecules to prevent bone loss.

While the above described countermeasures have been successful in minimizing to some extent the morbidity associated with abnormal bone cell function, the efficacy of such treatments is limited by the ability to appropriately deliver the active ingredient to the site where needed. In addition, most of these treatments have serious side effects when administered systemically.

Therefore, the need for site specific targeting of therapeutic agents has been felt. However, site-specific targeting requires quantitatively distinct receptors that are unique to bone. A few researchers have demonstrated that the inorganic component of bone which is comprised of hydroxyapatite (HAp), occurs normally only in hard tissues. A bisphosphonate, methylene bisphosphonate (MBP), is known for its predilection to bone sites undergoing remodeling, has been used in combination with Technetium-99 m ($^{99m}Tc$) as a non-therapeutic diagnostic imaging tool in the study of bone pathology (Davis and Jones, 1976; Lantto et al., 1987; Cronhjort et al., 1999). MBP has been studied as a bone matrix targeting moiety for osteotropic drug delivery. Fujisaki, et al., (1995; 1996), conjugated various model materials and pro-drug candidates to MBP and demonstrated their targeting efficacy in vivo. Estradiol conjugated to MBP was taken up in bone and then released from MBP either by enzymatic or chemical hydrolysis of the ester conjugation linkage. Uludag, et al., (2000a; 2000b), demonstrated the osteotropic delivery of model proteins conjugated to MBP by similar chemistry.

In addition, several bone non-collagenous proteins, such as osteopontin and bone sialoprotein, are known to contain amino residue sequences that bind specifically to HAp (Nagata et al., 1991). Fujisawa et al., determined that a six-residue aspartic acid oligopeptide ($Asp_6$) preferentially binds to the calcified matrix in vivo (Kasugai et al., 2000) and that this targeting ligand can deliver an estradiol pro-drug in vivo (Yokogawa et al., 2000).

Prior approaches for targeting bone that use simple molecules conjugated to bone-targeting ligands that preferentially accumulated in bone have serious drawbacks. First, conjugated molecules are systemically exposed and, therefore, are subject to rapid elimination or can have action on sites other than bone. Second, conjugation of the bone-targeting ligands to the therapeutic molecules can adversely alter their therapeutic activity. Lastly, release of the active molecule from the targeting ligand, and its subsequent activity, is dependent on the degradation kinetics of the conjugation linkage.

Nonetheless, the aging global population translates to ever-increasing demand for orthopedic countermeasures to skeletal deterioration resulting from the increasing fragility of skeletal structures with age. In addition, there is an acute need to find effective countermeasures for other bone conditions and ailments. There is, therefore, a great need in the art for novel therapeutic compositions that can be used to deliver therapeutic agents to targets in the bone for effective treatment of bone-associated maladies.

SUMMARY OF THE INVENTION

In one aspect, the invention provides enhanced techniques for bone-targeting comprising use of nanocapsule delivery vehicles. Encapsulation provides an opportunity to consider therapeutics that are efficacious in treating bone diseases, but that otherwise may be rapidly cleared from the system, only elicit a biological response in close proximity to target cells, be toxic to other cell phenotypes, or be systemically active. In certain aspects of the invention, the targeted delivery of therapeutic agents to the bone is extended by including the capabilities of controlled and triggered release of the therapeutic agents either through engineered degradation of the delivery vehicle or in response to localized stimuli.

Therefore, in one aspect of the invention, compositions that effectively target the systemic skeleton or bone tissues or bone cells that may further comprise one or more bioactive factors or therapeutic agents that are useful to treat or prevent bone-related disorders and conditions are provided.

Thus, in one aspect, the invention provides nanocapsules encapsulating at least a first bioactive factor, wherein the nanocapsule is bound to at least a first ligand having specificity for a component of the systemic skeleton.

In some embodiments of the invention, the ligand is surface bound to the nanocapsule. In yet other embodiments of the invention, the ligand has an affinity for hydroxyapatite in the systemic skeleton. In further embodiments of the invention, the ligand is a bisphosphonate. In specific embodiments of the invention, the ligand is methylene bisphosphonate (MBP), or analogues thereof, such as alendronic acid.

In some specific embodiments of the invention, the bisphosphonate has the structure:

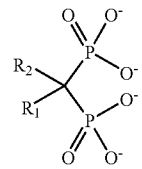

In other specific embodiments, the bisphosphonate is the MBP ligand, and is represented by the structure:

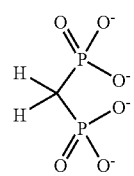

In additional embodiments of the invention, the ligand is an oligomer comprising one or more aspartic acid residues. In a specific embodiment of the invention, the ligand is an oligomer comprising six aspartic acid residues ($Asp_6$). In some embodiments of the invention, the $Asp_n$ ligand is represented by the structure:

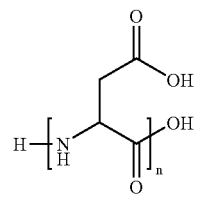

or has a molecular formula of $(C_4H_5O_3N)_n+H_2O$. In some specific embodiments of the invention, the formula weight for n=4 is 478.37 and for n=6 the formula weight is 708.55.

In other aspects of the invention, the ligand may be a protein, polypeptide, or a peptide. The protein, polypeptide, or a peptide may be one that has affinity for HAp. The peptide, polypeptide or protein may be either a positively charged or a negatively charged. It is also contemplated that the protein, polypeptide, or a peptide may comprise a sequence of bone sialoprotein or osteopontin or fragments thereof.

In one aspect of the invention, the range of content of the targeting ligands in the nanocapsules of the invention is in the order of about 0.1-10 mol %. Thus, one may use about 0.1 mol %, 0.2 mol %, 0.5 mol %, 1.0 mol %, 1.5 mol %, 2.0 mol %, 2.5 mol %, 3.0 mol %, 3.5 mol %, 4.0 mol %, 4.5 mol %, 5.0 mol %, 5.5 mol %, 6.0 mol %, 6.5 mol %, 7.0 mol %, 7.5 mol %, 8.0 mol %, 8.5 mol %, 9.0 mol %, 9.5 mol %, or about 10 mol % of the targeting ligand in a nanocapsule. Intermediate ranges such as, about 0.11 mol %, 0.56 mol %, or about 9.9 mol % and the like are also contemplated.

In other specific aspects of the invention, the nanocapsule has a diameter of from 1 nm to 200 nm. In non-limiting embodiments of the invention, the nanocapsule has a diameter of about 50 nm, about 100 nm, about 150 nm, or about 200 nm. It is contemplated that the nanocapsules of the invention may have diameters of about 10 nm, 20 nm, 30 nm, 40 nm, 60 nm, 70 nm, 80 nm, 90 nm, 110 nm, 120 nm, 130 nm, 140 nm, 160 nm, 170 nm, 180 nm, 190 nm as well as intermediates such as 5 nm, 15 nm, 17 nm, 38 nm, 240 nm and the like.

In some aspects of the invention, the nanocapsules may comprise a bioactive factor that can prevent or treat any bone-related disorder or condition. The use of any bioavctive factor known in the art to treat a bone-related condition may be used. In some embodiments of this aspect of the invention, the bioactive factor is a bone morphogenetic protein, a protein fragment, a peptide, estrogen, a bisphosphonate, TGF-β, a non-peptide small molecule, and an osteotropic agent. In other embodiments of the invention, the bioactive factor is an osteotropic agent. In still other embodiments of the invention, the bioactive factor is a peptide. In specific aspects of this embodiment of the invention, the peptide is hormonally active. In yet other embodiments of the invention, the bioactive factor is a protein. In still other embodiments of the invention, the bioactive factor is a non-peptide small molecule.

In some aspects of the invention, the nanocapsule is a liposome. In yet other aspects of the invention, the nanocapsule is a niosome. The use of different liposomes are contemplated. Thus, in some non-limiting embodiments of this aspect of the invention, the liposome is a metalized liposome, the liposome is unilamellar, or the liposome is micellar. In other aspects of the invention, the nanocapsule is a pillared construct. In yet other aspects of the invention, the nanocapsule is polymer-based. In still other aspects of the invention, the nanocapsule is a micelle. In some aspects of the invention, the nanocapsule is a nanotubule. The nanocapsules of the invention may be composed of inorganic materials or organic materials. In some specific aspects of the invention, the nanocapsules may be composed of lipids such as phospholipids.

In another aspect, the invention provides methods of delivering a bioactive factor to a component of the systemic skeleton of an individual in need thereof comprising: (a) obtaining nanocapsules comprising at least a first bioactive factor, wherein the nanocapsules further comprise at least a first ligand having specificity for a component of the systemic skeleton; and (b) administering the composition to the individual.

In some embodiments of the invention, the ligand is surface bound to the nanocapsules. In other embodiments of the invention, the ligand has an affinity for hydroxyapatite in the systemic skeleton. In yet other embodiments of the invention, the ligand a bisphosphonate exemplified by methylene bisphosphonate (MBP).

In further embodiments of the invention, the ligand is a bisphosphonate. In specific embodiments of the invention, the ligand is methylene bisphosphonate (MBP), or analogues thereof, such as alendronic acid. In some specific embodiments of the invention, the bisphosphonate has the structure:

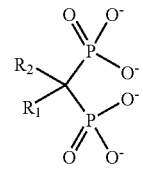

In other specific embodiments, the bisphosphonate is the MBP ligand, and is represented by the structure:

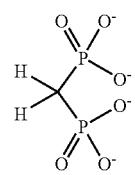

In additional embodiments of the invention, the ligand is an oligomer comprising one or more aspartic acid residues. In a specific embodiment of the invention, the ligand is an oligomer comprising six aspartic acid residues ($Asp_6$). In some embodiments of the invention, the $Asp_n$ ligand is represented by the structure:

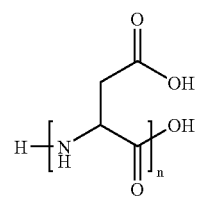

or has a molecular formula of $(C_4H_5O_3N)_n + H_2O$. In some specific embodiments of the invention, the formula weight for n=4 is 478.37 and for n=6 the formula weight is 708.55.

In other aspects of the invention, the ligand may be a protein, polypeptide, or a peptide. The protein, polypeptide, or a peptide may be one that has affinity for HAp. The peptide, polypeptide or protein may be a either a positively charged or a negatively charged. It is also contemplated that the protein, polypeptide, or a peptide may comprise a sequence of bone sialoprotein or osteopontin or fragments thereof.

In other aspects of the invention, it is contemplated that the composition further comprises a pharmaceutically acceptable carrier.

In some aspects of the invention, the bioactive factor is released from the nanocapsules upon contact of the nanocapsules with a signal released from the systemic skeleton.

In other aspects of the method of the invention set forth above, the step of obtaining is further defined as comprising obtaining a plurality of nanocapsules with different temporal release characteristics.

In some aspects of the invention, the nanocapsules of the invention have a diameter of from 1 nm to 200 nm. Thus, nanocapsules of about 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 run, 100 nm, 110 nm, 120 nm, 130 nm, 140 nm, 150 nm, 160 nm, 170 nm, 180 nm, 190 nm to about 200 nm may be used. In certain specific aspects the diameters of the nanocapsules is about 50 nm, about 100 nm, about 150 nm or about 200 nm.

In some aspects of the invention, the bioactive factor may be selected from the group consisting of a bone morphogenetic protein, a protein fragment, estrogen, a bisphosphonate, TGF-β, a non-peptide small molecule, and an osteotropic agent. Thus, in some embodiments of the invention, the bioactive factor is an osteotropic agent. In other embodiments of the invention, the bioactive factor is a peptide. In specific embodiments of the invention, the peptide is hormonally active. In yet other embodiments of the invention, the bioactive factor is a protein. In still other embodiments of the invention, the bioactive factor is a non-peptide small molecule.

In some aspects of the invention, the nanocapsule is a liposome. In yet other aspects of the invention, the nanocapsule is a niosome. The use of different types of liposomes is contemplated. Thus, in some non-limiting embodiments of the invention, the liposome is a metalized liposome, the liposome is unilamellar, or the liposome is micellar. In other aspects of the invention, the nanocapsule is a pillared construct. In yet other aspects of the invention, the nanocapsule is polymer-based. In still other aspects of the invention, the nanocapsule is a micelle. In some aspects of the invention, the nanocapsule is a nanotubule.

In some aspects, the nanocapsules of the invention may be composed of inorganic materials and/or organic materials. In some specific aspects of the invention, the nanocapsules may be composed of lipids such as phospholipids.

In one aspect of the invention, the patient or subject or individual to whom the composition is administered is one who is afflicted by a bone related disorder or condition. In other aspects of the invention, the patient or subject or individual is one who is at a risk of developing a bone related disorder or condition and therefore the method will be a preventive method for the prophylactic prevention of bone loss. Such prophylactic treatment may find use, for example, in preventing bone loss in individuals with a family history of a bone disorder or condition, and in preventing bone loss during manned spaceflights. Some non-limiting examples of bone-disorders and conditions afflicting patients or subjects that may be treated by the methods of the present invention include osteoporosis, osteoarthritis, Paget's disease, osteohalisteresis, osteomalacia, periodontal disease, bone loss resulting from multiple myeloma and other forms of cancer, bone loss steroid treatments, or bone fractures, and age-related loss of bone mass. The targeted nanocapsules of the invention can also be used to delivery other selected therapeutics to bone, including, for example, treatment of infection or tumors in bone via antibiotics or cancer therapies, respectively. Similarly, the nanocapsules of the invention may also find use in fracture repair therapies, prosthetic implants, cartilage repair, and tissue engineering applications.

Different methods of administering therapeutic compositions are known in the art and any such method may be used to deliver the therapeutic compositions of the present invention. In some non-limiting embodiments of the invention, the compositions may be administered locally, systemically or regionally. In other specific embodiments of the invention, the compositions may be administered intravenously, intra-arterially, topically, intranasally, or orally. Yet other methods of parenteral administration, such as muscular, sub-cutaneous, intraperitoneal, intralesionally, dermally, are also contemplated.

In another aspect, the invention also provides methods of preventing bone loss in a patient in need thereof comprising: (a) obtaining nanocapsules comprising at least a first osteotropic factor, wherein the nanocapsules further comprise at least a first ligand having specificity for a component of the systemic skeleton; and (b) administering the composition to the patient.

In one aspect of the invention, the ligand is surface bound to the nanocapsule. In another aspect of the invention, the ligand has an affinity for hydroxyapatite in the systemic skeleton.

In other aspects of the invention, the osteotropic factor is released from the nanocapsules upon contact of the nanocapsules with a signal released from the systemic skeleton. In yet other aspects of the invention, the "obtaining" is further defined as comprising obtaining a plurality of nanocapsules with different temporal release characteristics.

In further aspects of the invention, the ligand is a bisphosphonate. In specific embodiments of this aspect of the invention, the ligand is methylene bisphosphonate (MBP). In yet other specific aspects of the invention, the ligand has the following molecular formula:

In yet other embodiments of the invention, the ligand is a bisphosphonate exemplified by methylene bisphosphonate (MBP).

In further embodiments of the invention, the ligand is a bisphosphonate. In specific embodiments of the invention, the ligand is methylene bisphosphonate (MBP), or analogues thereof, such as alendronic acid. In some specific embodiments of the invention, the bisphosphonate has the structure:

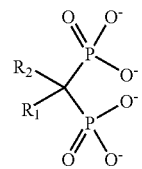

In other specific embodiments, the bisphosphonate is the MBP ligand, and is represented by the structure:

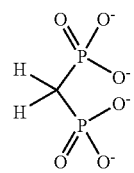

In additional embodiments of the invention, the ligand is an oligomer comprising one or more aspartic acid residues. In a specific embodiment of the invention, the ligand is an oligomer comprising six aspartic acid residues ($Asp_6$). In some embodiments of the invention, the $Asp_n$ ligand is represented by the structure:

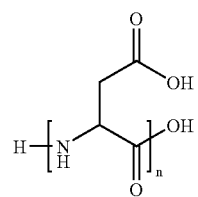

or has a molecular formula of $(C_4H_5O_3N)_n + H_2O$. In some specific embodiments of the invention, the formula weight for n=4 is 478.37 and for n=6 the formula weight is 708.55.

In other aspects of the invention, the ligand may be a protein, polypeptide, or a peptide. The protein, polypeptide, or a peptide may be one that has affinity for HAp. The peptide, polypeptide or protein may be a either a positively charged or a negatively charged. It is also contemplated that the protein, polypeptide, or a peptide may comprise a sequence of bone sialoprotein or osteopontin or fragments thereof.

In other aspects of the invention, the composition further comprises a pharmaceutically acceptable carrier.

In some aspects of the invention, the osteotropic agent is a peptide. In other aspects of the invention, the osteotropic agent is a nucleic acid. In still other aspects of the invention, the osteotropic agent is a protein. In yet other aspects of the invention, the osteotropic agent is a non-peptide small molecule.

In one aspects of the invention, the nanocapsule is a liposome. In other aspects of the invention, the nanocapsule is a niosome. The use of different liposomes are contemplated. Thus, in some non-limiting embodiments of the invention, the liposome is a metalized liposome, the liposome is unilamellar, or the liposome is micellar.

In some aspects of the invention, the nanocapsule is a pillared construct. In other aspects of the invention, the nanocapsule is polymer-based. In still other aspects of the invention, the nanocapsule is a micelle. In yet other aspects of the invention, the nanocapsule is a nanotubule.

In one aspect of the invention, the nanocapsules of the invention may be composed of inorganic materials or organic materials. In some specific aspects of the invention, the nanocapsules may be composed of lipids such as phospholipids.

In one aspect of the invention, the patient or subject to whom the composition is administered is one who is afflicted by a bone related disorder or condition. In other aspects, the patient or subject can be one who is at a risk of developing a bone related disorder or condition and therefore the method will be a preventive method. Some non-limiting examples of bone-disorders and conditions afflicting patients or subjects that are treatable or preventable by the methods of the present invention include osteoporosis, osteoarthritis, Paget's disease, osteohalisteresis, osteomalacia, periodontal disease, bone loss resulting from multiple myeloma and other forms of cancer, bone loss steroid treatments, or bone fractures, and age-related loss of bone mass.

Different methods of administering therapeutic compositions are known in the art and any such method may be used to deliver the therapeutic compositions of the present invention. In some non-limiting embodiments of the invention, the compositions may be administered locally, systemically or regionally. In other non-limiting embodiments of the invention, the compositions may be administered intravenously, intra-arterially, topically, orally. In still other embodiments of the invention, other methods of parenteral administration, such as muscular, sub-cutaneous, intraperitoneal, intralesionally, dermally, are also contemplated.

"A" or "an" is defined herein to mean one or more than one. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Targeting nanocapsules are introduced to the system by an appropriate means. The nanocapsules are comprised of a membrane encompassing, containing, or stabilizing a therapeutic payload. The nanocapsule membrane is covered with targeting ligands that will selectively bind to targeted sites located in bone. FIG. 1B. Targeting nanocapsules selectively bind to the hydroxyapatite component of the bone matrix via targeting ligands. FIG. 1C. The therapeutic payload is released following targeted site attachment.

FIG. 4A. Evolution of liposome particle size with decreasing extrusion pore size. Liposomes were extruded twice through 2 μm pores, four times through 0.4 μm pores and eight time through 0.1 μm pores. FIG. 4B Typical final liposome particle size distribution trace. Liposome size is 112.1 nm±μ23.8 nm.

DESCRIPTION OF ILLUSTRATIVE EMBODIMENTS

Figure 1A:
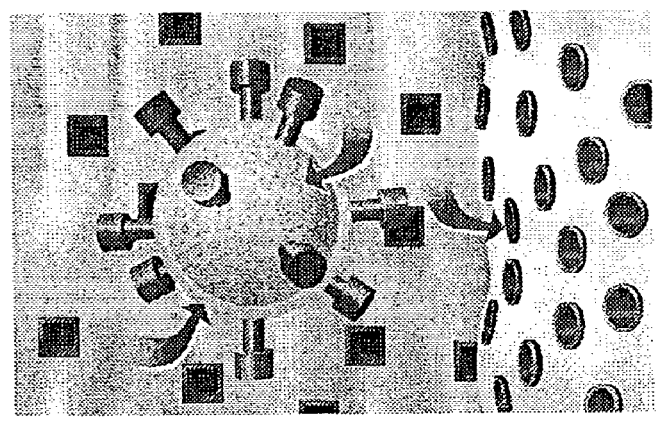
FIGS. 1A, 1B, & 1C.

The invention overcomes the deficiencies of the prior art by providing compositions comprising nanocapsules for the targeted delivery of therapeutic agents to the systemic skeleton. The compositions and methods of the invention can be used for the delivery of potentially any bioactive factor to bone. The bioactive factors are delivered in nanocapsules comprising a payload of the bioactive factor and that are targeted for specific delivery to bone. The nanocapsules can be delivered non-invasively as a therapeutic or as a countermeasure designed to prevent development of bone abnormalities. The invention has application for a variety of conditions associated with bone loss, bone abnormalities or bone damage including, but not limited to osteoporosis, osteoarthritis, Paget's disease, osteohalisteresis, osteomalacia, periodontal disease, bone loss resulting from multiple myeloma and other forms of cancer, bone loss resulting from side effects of other medical treatment (such as steroids), bone loss resulting from fractures, and age-related or weightlessness-related loss of bone mass.

By allowing targeted delivery of bioactive factors, the invention allows localized delivery of the bioactive factors at the site where the factors are needed, e.g., to the affected bone matrix. Localized delivery increases the potency without requiring an increase in the dosage, and also reduces side-effects incurred by systemic exposure. The nanocapsules of the invention can also be designed for controlled or triggered release of payloads, for example, by capsule degradation and payload diffusion or in response to external signals or physiologic signals occurring the bone microenvironment. This allows therapeutic release specifically to sites where treatment is needed. Targeted and/or timed delivery of bioactive factors also allows administration of a lower overall dose of the bioactive factor to the patient, minimizing the potential for adverse side effects due to narrow therapeutic-toxic windows.

The nanocapsule drug vehicles can be targeted by fabricating the nanocapsules to contain both surface-bound bone-specific targeting ligands and payloads comprising bioactive therapeutic agents, compounds or countermeasures. Such surface-bound bone targeting ligands can specifically target the bone mineral phase. Examples of targeting ligands that may be used include bisphosphonates and oligopeptides, which have been shown to preferentially bind to bone.

Targeting to bone can also be achieved by surface-functionalizing nanocapsules with hydroxyapatite (HAp) binding residues (e.g., bisphosphonates, peptide residues, etc.). Therefore, the nanocapsules can be comprised of targeting ligands, a membrane component and a therapeutic payload. The targeting ligands can be attached to a nanocapsule membrane and can selectively bind to targeted sites within the systemic skeleton.

One application of the invention is in the delivery of bioactive factors to maintain skeletal health by preventing bone loss. Such factors may prevent bone resorption, for example, to treat osteoporosis or as a maintenance program for the prophylactic prevention of bone loss. Such prophylactic treatment may find use, for example, in preventing bone loss during manned spaceflight. Bone mass loss is also a growing problem for the rapidly aging population, and could be prevented by administration of the targeted nanocapsules provided by the invention. One such bioactive factor that may be used is transforming growth factor beta (TGF-$\beta$), which activates cell proliferation and metabolic pathways in osteoblast-like cells in vitro. Other non-limiting examples of bioactive peptides that may be used are other sub-classes of the TGF-$\beta$ family of peptides and the bone morphogenetic proteins. Still other bioactive factors that may be used are compounds that stimulate expression of bone morphogenetic protein 2. Other non-limiting examples of such BMP-2 expression stimulators are statins. All these molecules are well known in the art.

Specific targeting of nanocapsules also allows targeting of skeletal structures, especially areas of high bone turnover (e.g., areas undergoing active resorption due to disease or non-loaded use). The targeted nanocapsules can also be used to delivery other selected therapeutics to bone, including, for example, treatment of infection or tumors in bone via antibiotics or cancer therapies, respectively. Similarly, the nanocapsules may also find use of fracture repair therapies and tissue engineering applications.

I. Targeted Delivery of Bioactive Factors

A. Proposed Countermeasure Methods

Figure 1B:
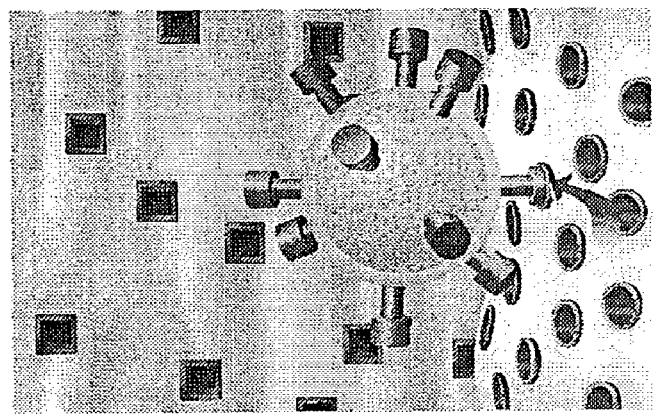
Figure 1C:
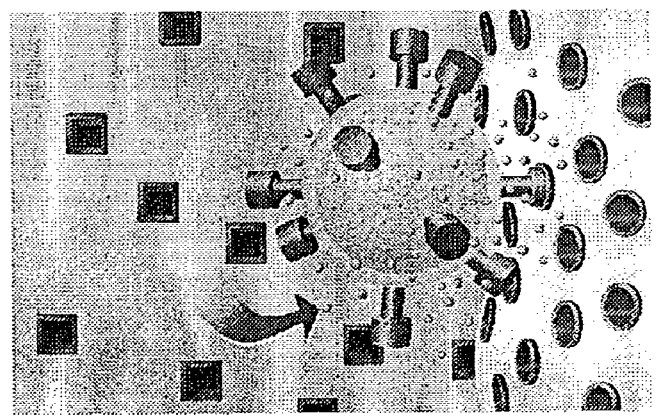

One aspect of the invention is set forth, for illustrative purposes only, in FIG. 1. In this approach, a bioactive factor is incorporated into a nanocapsule vehicle. The nanocapsule is designed to specifically target bone, for example, by targeting the hydroxyapatite (HAp) component of the skeletal matrix. In vivo, the targeted nanocapsules preferentially bind to exposed HAp surfaces (e.g., especially bone matrix locations undergoing osteoclastic resorption), whereupon they subsequently disrupt to release the therapeutic payload contained in the nanocapsules.

In a second approach, the nanocapsules may be designed to release their therapeutic payload temporally in response to a specific stimulus. This stimulus could be an externally applied signal, a complementary factor administered in schedule, or may be a biochemical signal present in the bone microenvironment. In this way, delivery can be made at locations where needed or otherwise appropriate. If the nanocapsules are not exposed to the appropriate signal or factor, the nanocapsules remain intact and are eventually expelled by the body through normal metabolic activities. Therefore, any side effects associated with the bioactive factor(s) contained in the nanocapsules may be avoided when treatment is not needed. Still further, lower effective doses of the bioactive factor in the locally affected bone microenvironment will be received by the patient when the treatment is needed.

The bioactive factor could be one or more of many agents that have been shown to impact the formation of new bone matrix (e.g., BMPs, protein fragments, statins, estrogens, molecular conjugates, etc.) or to have any other desired therapeutic or preventative effect with respect to any bone-associated malady. As indicated, the bioactive factors are encapsulated in nanocapsules (for example, liposomes, niosomes, self-assembled molecular cages, etc.) that may be designed to have controlled temporal release in the appropriate physiological environment. Some examples of bioactive factors that could be delivered with the invention include insulin-like growth factors (IGF), bone morphogenetic proteins (BMP), heparin-binding fibroblast growth factor (FGF), platelet-derived growth factors (PDGF), TGF-$\beta$, parathyroid hormone (PTH), fluoride, and statins.

The nanocapsules could be introduced systemically by intravenous injection or non-invasively by intranasal uptake, or topical application. In vivo, the nanocapsules would preferentially bind to exposed HAp surfaces (e.g., especially bone matrix locations undergoing osteoclastic resorption), whereupon they would subsequently disrupt to release their therapeutic payload.

B. Bone Loss

Figure 2:
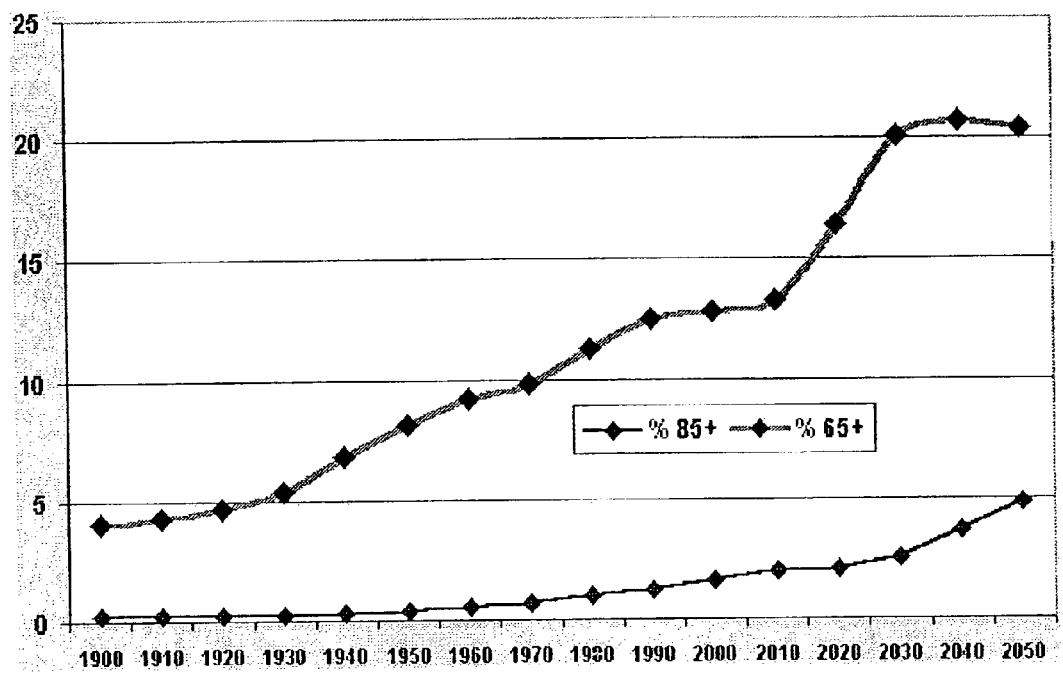
FIG. 2. Older population by age: 1900-2050 for the age groups 65+ and 86+ years of age (source: US Department of Health and Human Services, Administration on Aging).

As described above, one application of the methods of the invention is in the prevention or treatment of bone loss. The aging global population translates to ever-increasing demand for such countermeasures to skeletal deterioration resulting from the increasing fragility of skeletal structures with age. Demographic trends in the United States, Europe and Japan are similar, with the percentage of the population over the age of 65 increasing dramatically (FIG. 2) (see, e.g., US Department of Health and Human Services, Administration on Aging, www.aoa.dhhs.gov). This underscores the importance of the invention. Maintaining or restoring bone volume is therefore a major health care issue for an increasingly vast segment of the general population (see, e.g., Trends in Orthopedics, 2000; Orthopedic Industry, 2000). The need for a therapeutic protocol that targets the systemic skeleton to maintain and/or increase bone volume cannot be overstated.

Yet another application of this technology is with regard to fracture healing and prevention of bone loss during fractures. Targeted delivery of bone healing agents, such as anabolic agents, to the bone can minimize the time of bone-healing and also prevent loss of existing bone tissue. In addition, the invention is contemplated useful in the process of prosthetic fixation.

Another possible source of bone loss which could be treated with the invention is spaceflight. Astronaut health during long-term space flight is a major concern and central to this general health concern are the effects of space flight on skeletal tissues. Skeletal degradation can dramatically affect the ability to perform both rudimentary tasks and critical extravehicular activities during long-term space missions. Astronauts experience a 1-2% decrease in bone volume per month at selected skeletal sites and this bone loss is generally not fully recovered on return to Earth (*National Geographic*, January, 2001; Vico et al., 2000). This rate of bone volume loss could cause decreases in bone mineral density (BMD) of more than 50% during a 2-3 year Mars mission, significantly impairing an astronaut's abilities during space flight and on entry into gravitational environments. The consensus is that bone loss countermeasures are necessary for continued space exploration.

Knowledge of human adaptation to long-term space flight lags behind the technical knowledge required for such travel (Turner, 2000). Experience in near-earth space flight suggests that most biological effects on the skeletal system result from changes in physical loading of the skeleton. This stems from the fact that an astronaut in near-earth orbit, though still within the gravitational field, experiences free-fall as an adjunct of spacecraft velocity. Changes in bone biology and the associated loss in bone volume begin to occur within a few days after leaving Earth. MIR space station studies clearly show that individuals experience decreases in BMD in load-bearing areas such as the lumbar spine, proximal femur, and calcaneus, while non-load-bearing areas, such as the cranium, distal radius, and ribs, experience increases in BMD (McCarthy et al., 2000). Experiments have shown a decrease in the expression of selected bone matrix cytokines (Carmeliet et al., 1998), such as TGF-β and insulin-like growth factor-1 (IGF-1), both of which are known to regulate bone formation (Mundy, 1996). Similar findings have been reported in cell culture studies wherein osteoblast activity and associated deposition of new skeletal matrix both decrease. Thus, it is clear that the normal bone remodeling process is profoundly altered during space flight. Osteoblastic bone formation decreases and osteoclastic resorption activity either remains unchanged or slightly increases. The net result is the onset of osteopenia (Holick, 2000).

Infusion of IGF-1 stimulates bone growth in normally loaded bones but in unloaded bones, an extremely high dose of 2 mg/kg/day is required to demonstrate any protective effect against unloading (Bikle et al., 1994). Decreases in TGF-β message levels have been observed in three different models of skeletal unloading: spaceflight, sciatic neurotomy, and hindlimb unloading (Westerlind and Turner, 1995). These results are consistent with a growing body of evidence suggesting that reduced bone formation during spaceflight is due to decreased osteoblast function (Harris et al., 2000). Significantly, infusion of TGF-β (2 µg/kg/day) corrects the decrease in bone mass, calcium content, osteoblast number and mineralization rate induced by hindlimb unloading in rats, but has no effect on bone formation in control animals. Further, TGF-β infusion decreases the indices of bone resorption in both normal and unloaded rats (Machwate et al., 1995). Effective targeting and delivery of TGF-β to increased concentrations locally in the bone microenvironment would be a desirable goal of any drug delivery countermeasure (Mundy, 2000).

C. Targeted Delivery of Nanocapsules

Targeted delivery of therapeutics via nanocapsules can occur by either passive or active mechanisms. Passive targeting occurs when nanocapsules extravasate through damaged vasculature to accumulate in tumors and inflamed tissues (Wu et al., 1993). Accumulation increases by improving circulation half-life and by preventing nanocapsules interaction with serum components. In contrast, active targeting is achieved through specific interaction between nanocapsule-bound or -associated ligands and complementary binding agents at the targeted site. This approach has clear opportunity for improved, efficacious delivery of biactive agents, since many do not target bone, have narrow therapeutic-toxic windows when administered systemically, and require close proximity to target cells to exert their biological activity.

Prior techniques employing liposome-based targeting approaches have used one of a handful of methods, including receptor targeting, cell adhesion molecules, extracellular matrix molecules, selecting, and antibody ligands (Forssen and Willis, 1998). Lee and Huang (1995) demonstrated a 45-fold increase in doxorubicin uptake from folate-modified liposomes in to epithelial cancer cells, which over-express folate receptors. Kamps, et al. (1997), demonstrated that liposomes modified with anionized albumin were taken up by hepatic endothelial cells, whereas nearly all non-modified liposomes remained in circulation 30 minutes post-injection.

Bone offers several potential sites for targeted delivery of bioactive agents. Bone is a composite matrix comprised of organic and inorganic constituents. The organic portion of the matrix consists of a mixture of collagen, bone proteins, water, and cells (Rho et al., 1998). The inorganic portion of the matrix consists chiefly of hydroxyapatite (HAp). While it is possible to selectively bind bioactive constituents to specific receptors located either on bone cells or on bone proteins, such targeting may not be sufficiently specific. Similar receptors may exist on other cell phenotypes and many bone proteins can be found external to the bone matrix. Site-specific targeting requires targeting receptors quantitatively distinct from receptor sites found in other tissues. For this reason, HAp, which occurs normally only in hard tissues, provides one attractive targeting site for the selective delivery of bioactive agents to bone.

1. Targeting Ligands

In certain aspects of the invention, ligands having an affinity with bone are linked to nanocapsules. Two ligands in particular that may be used for targeting of nanocapsules to, for example, the HAp portion of the bone matrix without an associated therapeutic effect are methylene bisphosphonate (MBP) and an aspartic acid peptide residue. MBP is well known for its predilection to bone remodeling sites. For this reason, it has been used extensively in combination with Technetium-99m ($^{99m}Tc$) as a diagnostic imaging tool in the study of bone pathology (Davis and Jones, 1976; Lantto et al., 1987; Cronhjort et al., 1999). MBP has further been studied as a bone matrix-targeting moiety for osteotropic drug delivery. Fujisaki, et al., (1995 and 1996) have conjugated various model materials and prodrug candidates to MBP and demonstrated their efficacy in vivo. Estradiol conjugated to MBP has been shown to be rapidly taken up in bone and then to be released from MBP either by enzymatic or chemical hydrolysis of the ester conjugation linkage. Uludag, et al. (2000), have demonstrated the osteotropic delivery of model proteins conjugated to MBP by similar chemistry. The chemical formula for MBP is given below:

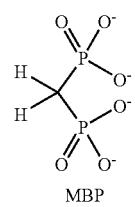

MBP

Several bone noncollagenous proteins, such as osteopontin and bone sialoprotein, are also known to contain amino residue sequences that bind specifically to HAp. For

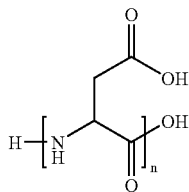

example, Fujisawa, et al., determined that a six-residue aspartic acid oligopeptide ($Asp_6$) would preferentially bind to the calcified matrix in vivo (Kasugai et al., 2000). They further showed that this targeting ligand could deliver an estradiol prodrug in vivo (Yokogawa et al., 2000). The chemical formula of this targeting ligand is given below:

$(Asp)_6 n=6$

Figure 3:
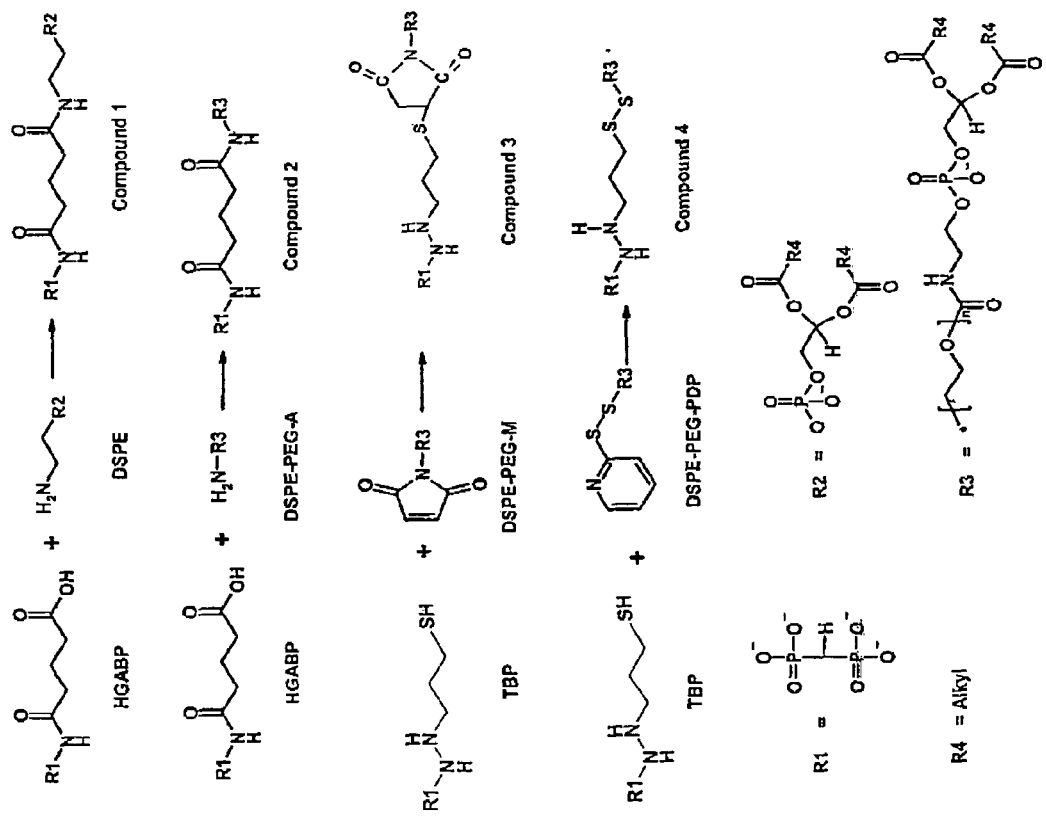
FIG. 3. Synthesis pathways to attach targeting-ligands to either phospholipids or PEGylated phospholipids.

Yet another ligand that could be used is 1-amino-1,1-diphosphonate methane (ABP). The amino functionalized analogue of methylene diphosphonate can be synthesized by published methods (Kontoci et al, 1996) as modified by Uludag, et al (2000). Once synthesized, the molecular structure of ABP can be confirmed by 1H, 13C, and 31P NMR. A description of the technique for synthesis of ABP-phospholipid and ABP-PEGylated phospholipid conjugates is set forth in FIG. 3 and Example 1. Still another ligand that can be used is alendronic acid.

2. Linking Targeting Ligands to Nanocapsules

Bifunctional cross-linking reagents represent one means for attaching a targeting ligand to a nanocapsule that may be used with the invention. Bifunctional cross-linking reagents have been extensively used for a variety of purposes including preparation of affinity matrices, modification and stabilization of diverse structures, identification of ligand and receptor binding sites, and structural studies and can be used for linking targeting agents to nanocapsules. Homobifunctional reagents that carry two identical functional groups have proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to nanocapsules are described in U.S. Pat. No. 5,603,872 and U.S. Pat. No. 5,401,511, each specifically incorporated herein by reference in its entirety. Various ligands can be covalently bound to a nanocapsule surface through the cross-linking of amine residues. The inclusion of phosphatidylethanolamine (PE) in a liposome provides an active functional residue, a primary amine, on the liposomal surface for cross-linking purposes.

Ligands can be bound covalently to discrete sites on nanocapsule surfaces. The number and surface density of these sites will be dictated by the nanocapsule type. The nanocapsule surfaces may also have sites for non-covalent association. To form covalent conjugates of ligands and nanocapsule, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and nanocapsules is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 1 details examples of certain hetero-bifunctional cross-linkers that may be used in accordance with the invention.

TABLE 1

Hetero-Bifunctional Cross-Linkers

| Linker | Reactive Toward | Advantages and Applications | Spacer Arm Length\ after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary ammes Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |

TABLE 1-continued

Hetero-Bifunctional Cross-Linkers

| Linker | Reactive Toward | Advantages and Applications | Spacer Arm Length\ after cross-linking |
|---|---|---|---|
| ABH | Carbohydrates Nonselective | Reacts with sugar groups | 11.9 A |

It has been shown that surface-bound targeting ligands can be shielded by other liposome components or surface-adsorbed species (Allen et al., 1995). However, recent research has shown that when targeting ligands are tethered to surface-bound spacers, the probability of these ligands to capture binding sites and the distance at which site recognition occurs are both increased as the tether length is increased (Jeppesen et al., 2001).

II. Nanocapsules

In certain aspects of the invention, nanocapsules are provided which are targeted to bone. Potentially any type of nanocapsule could be used. For example, liposomes or carbon-based cage structures could be used. Cage-like structures can be formed of, for example, ultrafine fullerene such as $C_{60}$ crystallite having diameters in the range of 5 to 50 nm. Bioactive payloads, such as agents that heal fractures, prevent bone loss, build bone tissue etc., are enclosed in these structures. Methods for producing the structures are disclosed in U.S. Pat. No. 5,648,056, the entire disclosure of which is specifically incorporated herein by reference. Nanocapsules may also be formed of charged particles of materials including clay and other pillared compounds, which can be linked with short-chain linking molecules to form secondary cage-like strictures. Similarly, niosomes may be used. Some methods for producing niosomes are described in U.S. Provisional Patent Application Ser. No. 60/351,701, filed Jan. 24, 2002 and entitled "Compositions and Methods for Targeted Drug Delivery" the entire disclosure of which application is specifically incorporated herein by reference.

A. Liposomes

In certain embodiments of the invention, liposomes could be used as nanocapsules. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

Liposomes can range in size from several nanometers to several micrometers in diameter. Liposome morphological types are broadly categorized as either multilamellar, unilamellar or micellar. Typically, small unilamellar vesicles (SUV) find application in drug delivery applications. The formulation, preparation, stability, and utility of the various liposome types have been the topic of considerable research culminating in several liposome-based drug formulations (Forssen and Willis, 1998). The key to success of liposome-based therapies has been the choice of the lipid components to achieve vesicle stability and the improvement in liposome circulation half-life in vivo.

Liposomes are inherently thermodynamically unstable due to both the high radius of curvature of the lipid bilayer and inefficient packing of the phospholipids (Lasic, 1996). The constituent phospholipids exhibit a gel-liquid crystalline phase transition temperature ($T_c$), below which the lipids are organized in a lamellar gel state. Stable liposomes are most commonly comprised of phospholipids having a $T_c$ well above physiologic temperatures. Similarly, phospholipid type plays a role in the fluidity of the lipid bilayer. The naturally occurring phospholipids, such as egg-derived phosphatidylcholine, produce more fluid bilayers, while synthetic phospholipids, such as distearoylphosphatidylcholine, produce more ridge bilayers. This stems from differences in the saturation of the pendent alkyl chains of the natural and synthetic phospholipids. It has been shown that liposomes with ridge bilayers significantly reduce the burst release of encapsulated proteins in vivo (Van Slooten et al., 2001).

Bilayer additives, such as cholesterol and α-tocopherol, further improve liposome stability by essentially filling and hardening the lipid bilayer. These additives also decrease bilayer permeability (Gregoriadis and Davis, 1979), reduce phospholipid exchange (Kirby et al., 1980), and increase oxidation stability, making liposomes viable drug delivery candidates. However, in vivo, liposomes exhibit short circulation longevity due to both bilayer lipid exchange with systemic lipids and rapid elimination by the reticuloendothelial system (RES). Short longevity results in decreased therapeutic effects of encapsulated drugs. Allen, et al. (1991), developed liposomes containing PEGylated phospholipid conjugates and showed that these vesicles greatly improved circulation half-lives by effectively introducing steric hindrance barriers to liposome breakdown.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In other embodiments, phospholipids from natural sources, such as egg or soybean phosphatidylcholine, brain phosphatidic acid, brain or plant phosphatidylinositol, heart cardiolipin and plant or bacterial phosphatidylethanolamine could be used, although are generally preferably not used as the primary phosphatide, i.e., constituting 50% or more of the total phosphatide composition or a liposome, because of the instability and leakiness of the resulting liposomes.

In particular embodiments, a bioactive factor may be, for example, encapsulated in the aqueous interior of a liposome, interspersed within the lipid bilayer of a liposome, attached to a liposome via a linking molecule that is associated with both the liposome and the bioactive factor, entrapped in a liposome, complexed with a liposome, etc.

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the bioactive factor and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with a suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In accordance with the invention, it will be desired that nanocapsules are sufficiently small to cross the blood vessel wall. Such nanocapsules will generally have a size of about 100 nm or smaller, including about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Mayhew et al., 1984; each incorporated herein by reference).

A liposome suspended in an aqueous solution is generally in the shape of a spherical vesicle, having one or more concentric layers of lipid bilayer molecules. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures.

Once manufactured, lipid structures can be used to encapsulate bioactive factors for targeting to bone, as is described herein. Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

B. Timed or Triggered Release of Nanocapsule Payloads

In certain embodiments of the invention, the use of nanocapsules designed for sustained, triggered or timed release is contemplated. For example, nanocapsules may be designed to release payloads of bioactive factors upon contact with a given signal, for example, that is released by bone. In this way, nanocapsule payloads are targeted not only to bone but also to bone in need of treatment with the given bioactive factor. Such a signal could be endogenous or externally administered. An external signal could be used to cause release of the nanocapsule payloads by, for example, using a chemical signal or physical signal. Examples of physical signals include administration of ultrasound or heat. In this manner the signal could be administered only to the site where treatment with the bioactive factor is needed, maximizing delivery of the factor to the site where needed and minimizing exposure to other parts of the body. Sustained release nanocapsule formulations could also be used. In this manner the efficacy of treatment may be maximized by maintaining therapeutic levels of the bioactive factor over time, without the need for continual administrations of the nanocapsules.

Temporally pulsed release of nanocapsules is also specifically contemplated. This could be achieved, for example, by administration of several types of nanocapsules having different delayed release characteristics. Such temporally pulsed techniques may yield benefits beyond those available with sustained release formulations. For example, increased bone matrix generation activity is observed in systems subjected to periodic exposure to bioactive factors in contrast to systems subjected to sustained exposure to the bioactive factor. This increased matrix generation may be due to the unhindered completion of the natural matrix generation cascade triggered by a spiked dosage of bioactive factor at the site. Also, sustained release may cause a physiologic acclimation that suppresses the triggered response to the spiked elevations in the bone factor concentration.

C. Kits

Nanocapsules prepared in accordance with the invention may be comprised in a kit. In a non-limiting example, nanocapsules targeted to bone and containing payloads comprising one or more bioactive factors may be comprised in a kit. The kits will thus comprise, in suitable container means, nanocapsules of the present invention.

The kits may comprise the nanocapsules in a suitably aliquoted composition of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also will generally contain a second, third or other additional container into which the additional components may be separately placed. However, various combinations of components may be comprised in a vial. The kits of the present invention also will typically include a means for containing the nanocapsules and any other reagent containers in close confinement for commercial sale. Such containers may include injection or blow-molded plastic containers into which the desired vials are retained.

Therapeutic kits of the present invention may include pharmaceutical compositions for delivery of bioactive factor-containing nanocapsules targeted to bone. Such kits will generally contain, in suitable container means, a pharmaceutically acceptable formulation of nanocapsules. The kit may have a single container means, and/or it may have distinct container means for each compound.

When the components of the kit are provided in one and/or more liquid solutions, the liquid solution is an aqueous solution, with a sterile aqueous solution being particularly preferred. The nanocapsule compositions may also be formulated into a syringeable composition. In which case, the container means may itself be a syringe, pipette, and/or other such like apparatus, from which the formulation may be injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the ultimate nanocapsule containing composition within the body of an animal. Such an instrument may be a syringe, pipette, forceps, and/or any such medically approved delivery vehicle.

III. Pharmaceutical Compositions

In certain aspects of the current invention, pharmaceutical compositions are provided for delivering nanocapsules containing bioactive factors to patients or subjects in need thereof. Pharmaceutical compositions of the present invention thus comprise an effective amount of one or more bioactive factors contained in nanocapsules in addition to any other desired components dissolved or dispersed in a pharmaceutically acceptable carrier.

An "effective amount" is the amount of an bioactive or therapeutic compound, agent or factor that is sufficient to treat or prevent a bone related condition or disease associated in a patient or subject. Thus and "effective amount" is one that preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems such as those described in the examples or any of those known to one of skill in the art.

The phrases "pharmaceutical or pharmacologically acceptable" refers to molecular entities and compositions that do not produce an adverse, allergic or other untoward reaction when administered to an animal, such as, for example, a human, as appropriate. The term "bioactive factor" or "is intended to refer to a chemical entity, whether in the solid, liquid, or gaseous phase which is capable of providing a desired therapeutic effect when administered to a subject in accordance with the invention. The term "bioactive factor" includes synthetic compounds, natural products and macromolecular entities such as polypeptides, polynucleotides, or lipids and also small entities such as neurotransmitters, ligands, hormones or elemental compounds. The term also includes such compounds whether in a crude mixture or purified and isolated.

The preparation of a pharmaceutical composition that contains at least one nanocapsule or other ingredients will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the nanocapsules of bioactive factors, its use in the therapeutic or pharmaceutical compositions is contemplated.

The nanocapsule-containing pharmaceutical composition may be comprised in different types of carriers depending on whether it is to be administered in solid, liquid or aerosol form, and whether it need to be sterile for such routes of administration as injection. The nanocapsules can potentially be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). In certain aspects of the invention, non-invasive administration techniques in particular may be used advantageously, for example, intranasal administration.

The actual dosage amount of a pharmaceutical composition of the present invention administered to a patient can be determined by physical and physiological factors such as body weight, severity of condition, the type of disease being treated, previous or concurrent therapeutic interventions, idiopathy of the patient and on the route of administration. This amount may also be adjusted based on the targeting agent used for the nanocapsules. One advance of the current invention is that targeting allows usage of doses lower than required using non-targeted treatments.

The practitioner responsible for administration will, in any event, determine the concentration of bioactive factor(s) and nanocapsules in a composition and appropriate dose(s) for the individual subject. In certain embodiments, pharmaceutical compositions may comprise, for example, an overall concentration of at least about 0.1% of an active compound, including, for example, about 0.1% to about 75%, 0.1% to about 50%, 0.1% to about 25%, 0.1% to about 10%, 0.1% to about 5%, 0.1% to about 3%, 0.1% to about 1%, 1% to about 10% and about 5% to about 15%.

In other non-limiting examples, a dose may also comprise, in nanocapsule carriers, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, and about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered in nanocapsule payloads, based on the numbers described above.

In addition to nanocapsules, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The bioactive factor that is used may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the nanocapsule composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. It will be necessary that such a carrier does not disrupt the nanocapsules prior to delivery to a patient. The proper fluidity of the composition can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In some cases, it will be preferable to include isotonic agents, such as, for example, sugars, sodium chloride or combinations thereof In other embodiments of the invention, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the nanocapsules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain further embodiments an oral composition may comprise one or more binders, excipients, disintegration agents, lubricants, flavoring agents, and combinations thereof. Such a composition may comprise, for example, one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating bioactive factors, e.g., in nanocapsules, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Nanocapsules can generally entrap compounds in a stable and/or reproducible way. To avoid side effects due to intracellular polymeric overloading, such ultrafine particles (sized around 0.1 µm) should be designed using polymers able to be degraded in vivo. Biodegradable polyalkyl-cyanoacrylate nanocapsules that meet these requirements are contemplated for use in the present invention, and/or such particles may be easily made.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and Conjugation of Targeting Ligands

For targeting Compound 1,1-amino-1,1-diphosphonate methane (ABP) is conjugated to distearoylphosphatidylethanolamine (DSPE, Avanti Polar Lipids, Alabaster, Ala.) using amide condensation chemistry. ABP can be synthesized by published methods (Kontoci et al, 1996) as modified by Uludag, et al (2000). ABP is converted to hemiglutarylamidomethylene bisphosphonate (HGABP) in preparation for conjugation by reaction with glutaric anhydride using the techniques described by Fujisaki, et al (1997). For Compound 2, HGABP is conjugated to DSPE-N-methoxypolyethylene glycol-2000 amine (DSPE-PEG-A, Avanti) by similar amide condensation chemistry. Alternatively, two alternative conjugation pathways may be used. In the first method (Compound 3), ABP is converted to the thiol analogue (TBP) by reaction with 2-iminothiolane (2-IT) according to chemistry described by Uludag, et al (2000). TBP is then conjugated with DSPE-N-methoxypolyethylene glycol-2000 maleimide (DSPE-PEG-M, Avanti) (Fleiner et al, 2001). Alternatively (Compound 4), TBP is reacted with DSPE-N-methoxypolyethylene glycol-2000 pyridyl-dithioproprionate (DSPE-PEG-PDP, Avanti) (Forssen and Willis, 1998). A description of the technique for synthesis of ABP-phospholipid and ABP-PEGylated phospholipid conjugates is set forth in FIG. 3.

The Asp6 targeting oligopeptide is prepared by the peptide synthesis method of Merrifield (1963) as modified by Kasugai, el al (2000). This molecule can also be purchased from Sigma as can Asp2, Asp3, and Asp4. For synthesis of Asp6-phospholipid and Asp6-PEGylated phospholipid, Asp6 is conjugated to DSPE (Avanti) and DSPE-PEG-A (Avanti) using methods described above for the conjugation of MBP. The structures of all synthesized compounds can be verified by spectroscopic methods. For example, an NMR spectrum of AMB and a MALDI spectrum of DSPE-$PEG_{2000}$-alendronate were performed by the inventor to verify synthesis.

Figure 5:
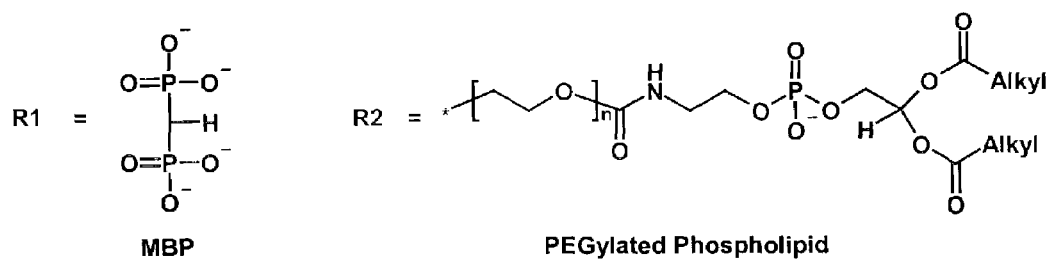
FIG. 5. Phospholipid conjugation strategy to attach MBP to a phospholipid. This strategy is the same for $Asp_6$ oligopeptide, in which conjugation is done through the N-terminus.
Figure 5:
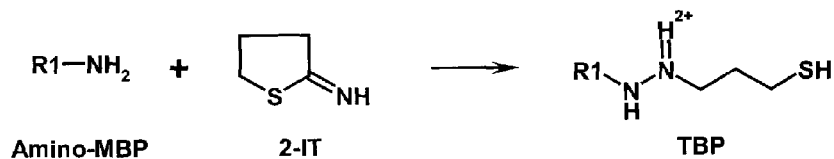
Figure 5:
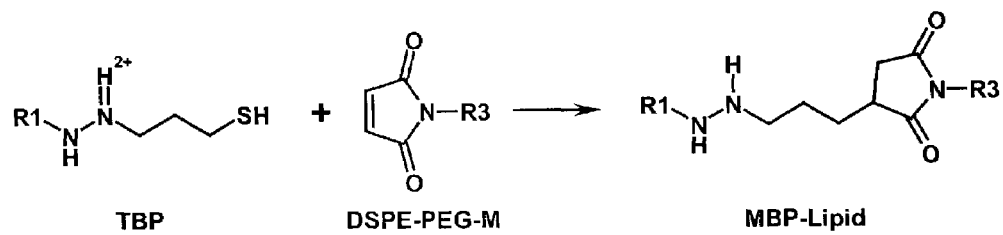

Conjugation strategies for attaching specific bone-targeting ligands to lipid components are illustrated in FIG. 5. The MBP-lipid conjugate was prepared by first forming the amino-functionalized analogue of MBP according to the method of Uludag, et al. (2000a; 2000b). Amino-MBP was thiolated by reaction with 2-iminothiolane (Traut's reagent) and subsequently reacted with maleimide functionalized DSPE-$PEG_{2000}$. The product was purified and analyzed by MALDI-TOF/MS. The $Asp_6$-lipid conjugate was prepared in a similar fashion. The oligopeptide was obtained commercially and the N-terminus thiolated by reaction with Traut's reagent to provide a reactive end for conjugation to the functionalized lipid. The resultant conjugate structure was confirmed by MALDI-TOF/MS.

Example 2

Preparation of Liposome Formulations

Figure 4A:
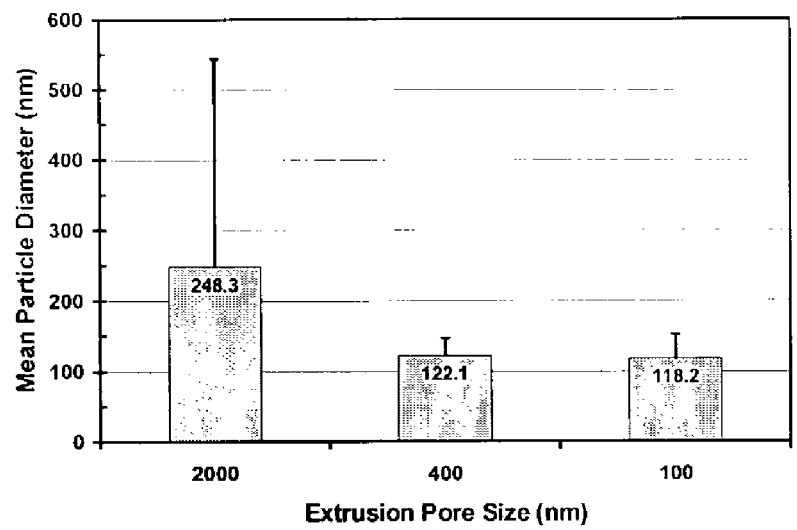
FIGS. 4A & 4B.
Figure 4B:
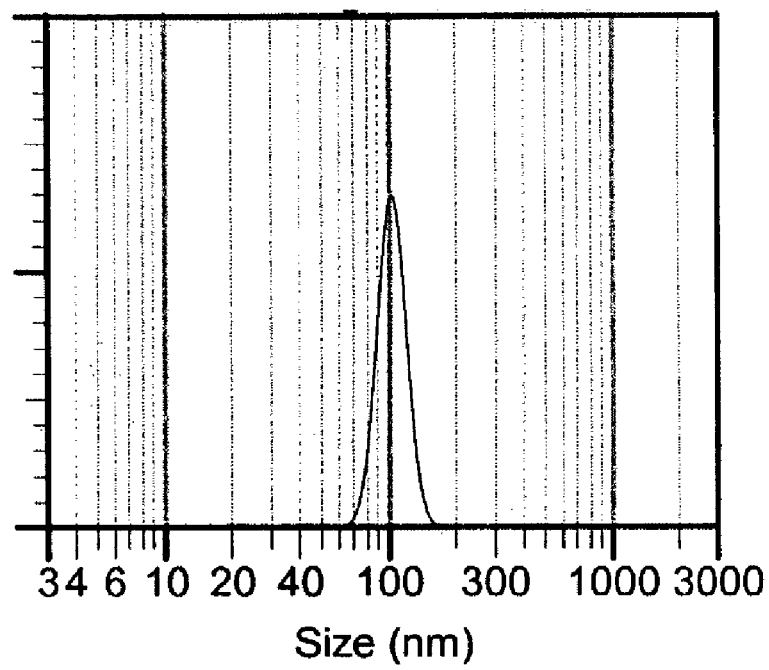

Liposomes are prepared by the film hydration method followed by sizing (Preparation of Liposomes, www.avantilipids.com (Mayer et al, 1986) as modified herein. Lipid formulations are dissolved in a mixture of methanol:chloroform (1:9 v/v) at a concentration of 10-20 mg/ml of solvent. The solution is vacuum-dried to a film onto the surface of a round-bottom flask using a rotary evaporator. The dried lipid film is heated to lipid transition temperature (Tc) and rehydrated using a sucrose-modified phosphate-buffered saline to yield large multilamellar vesicles (MLV). Small unilamellar vesicles (SUV) are then prepared from the hydrated lipids by a two-step procedure. The MLVs are first subjected to several freeze-thaw cycles by immersion in liquid nitrogen followed by thawing in a 40° C. water bath. This step increases liposome encapsulation efficiency (Mayer et al, 1985). These MLV preparations are pre-screened through a 2 µm polycarbonate filter and then repeatedly extruded through 0.1 µm polycarbonate filters with the aid of applied pressure. Extrusions are also conducted at the Tc. The SUVs are separated from the mother liquid by centrifugation and suspended in fresh PBS. The resulting SUVs are stored at 4° C. until required, usually within about one week. Liposome particle size can be determined by dynamic light scattering, negative-staining electron microscopy, or photon correlation spectroscopy. FIG. 4A depicts the mean diameter of the liposome particles as a function of extrusion pore size and FIG. 4B depicts the particle size distribution by this method.

In one embodiment, the liposome has a composition with a molar ratio of DSPC:Chol: α-tocopherol:DSPE-PEG$_{2000}$ : 1:1:0.04:0.05. At this point, the liposomes thus produced can be converted to targeting liposomes by incorporation of ligand-lipid conjugates as described in subsequent examples. Alternatively, the procedure just described can be modified to include a desired amount of ligand-lipid conjugate to obtain targeting liposomes.

A. Sizing of Lipid Suspension

Liposomes were sized according to the instructions at www.avantilipids.com ("Preparation of Liposomes"; Mayer et al, 1986) as modified herein. The technique and considerations in carrying out this methodology are as follows.

Disruption of LMV suspensions using sonic energy (sonication) typically produces small, unilamellar vesicles (SUV) with diameters in the range of 15-50 nm. The most common instrumentation for preparation of sonicated particles are bath and probe tip sonicators. Cup-horn sonicators, although less widely used, have successfully produced SUV. Probe tip sonicators deliver high energy input to the lipid suspension but suffer from overheating of the lipid suspension causing degradation. Sonication tips also tend to release titanium particles into the lipid suspension which must be removed by centrifugation prior to use. For these reasons, bath sonicators are the most widely used instrumentation for preparation of SUV.

Sonication of an LMV dispersion is accomplished by placing a test tube containing the suspension in a bath sonicator (or placing the tip of the sonicator in the test tube) and sonicating for 5-10 minutes above the Tc of the lipid. The lipid suspension should begin to clarify to yield a slightly hazy transparent solution. The haze is due to light scattering induced by residual large particles remaining in the suspension. These particles can be removed by centrifugation to yield a clear suspension of SUV. Mean size and distribution is influenced by composition and concentration, temperature, sonication time and power, volume, and sonicator tuning. Since it is nearly impossible to reproduce the conditions of sonication, size variation between batches produced at different times is not uncommon. Also, due to the high degree of curvature of these membranes, SUV are inherently unstable and will spontaneously fuse to form larger vesicles when stored below their phase transition temperature.

Lipid extrusion can also be used to size particles. Lipid extrusion is a technique in which a lipid suspension is forced through a polycarbonate filter with a defined pore size to yield particles having a diameter near the pore size of the filter used. Prior to extrusion through the final pore size, LMV suspensions are disrupted either by several freeze-thaw cycles or by prefiltering the suspension through a larger pore size (typically 0.2 µm-1.0 µm). This method helps prevent the membranes from fouling and improves the homogeneity of the size distribution of the final suspension. As with all procedures for downsizing LMV dispersions, the extrusion are performed at a temperature above the Tc of the lipid. Attempts to extrude below the Tc are typically unsuccessful as the membrane has a tendency to foul with rigid membranes which cannot pass through the pores. Extrusion through filters with 100 nm pores typically yields large, unilamellar vesicles (LUV) with a mean diameter of 120-140 nm. Mean particle size also depends on lipid composition and is quite reproducible from batch to batch.

Example 3

Encapsulation of Active Factors in Liposomes

The compounds to be delivered by nanocaspules, for example, bioactive factors, are encapsulated into liposome formulations using the method of Thérien and Shahum (1998). Briefly, the dried lipid film is rehydrated with a sucrose-PBS buffer and protein solution. The bioactive factors are then introduced. The concentration of bioactive factors will approximate standard dosages for the given bioactive factor, as will be well known to those of skill in the art. For example, BMP-2 is introduced at 50 µg/ml. For controls, BSA is introduced at about 10 mg/ml. The liposomes are sized and the free protein or bioactive factor is separated by ultracentrifugation (2×40 min, 4° C., 30,000 g). The pellet is redispersed in buffer and stored at 4° C.

To optimize liposome formulation and to increase the incorporation of the bioactive molecule, which in several instances is a protein or peptide, electrostatic interactions between positively charges amino acids on proteins and negatively charged lipids molecules is effectively used. For example, Van Slooten, et al. (2001), showed that negatively charged phospholipids, such as dialkyl-phosphatidylglycerol, significantly improved liposome-protein association efficiency, whereas positively charged phospholipids detrimentally impacted liposome-protein association efficiency. Other factors that affect encapsulation efficiency are bilayer surface charge and the ionic strength of the suspending media.

A base liposome formulation was prepared to encapsulate bovine serum albumin (BSA) as a control protein. BSA is 66.5 kDa in size, more than twice as large as natural anabolic proteins such as transforming growth factor beta and considerably larger than small molecule anabolic agents. BSA was encapsulated by introducing solubilized protein during lipid hydration prior to sizing. This results in BSA entrapped in liposomes as well as adsorbed on the surface of the liposomes and in the mother liquid. Quantification of BSA in the three locations by the bicinchoninic acid (BCA) protein assay using a BCA protein assay kit indicates it is distributed 25%/57%/18% encapsulated, surface adsorbed, and in solution, respectively. The liposome compositions are typically about 30 µg BSA/µmol of lipid as determined by the method of Stewart. At this point, the payload-containing liposomes can be converted to targeting liposomes using methods described in subsequent examples.

Example 4

Preparation of Targeting Liposomes

Targeting liposomes are typically prepared by the method of post-insertion, since this results in bone-targeting ligands located exclusively on the surface of the nanocapsule and eliminates possible deleterious interactions between the targeting ligands and the liposome payload (Allen et al., 1996; Allen et al., 1999; Uster et al., 2002). Essentially, micelles of ligand-lipid conjugates are incubated with preformed liposomes at elevated temperature whereupon the conjugates transfer from the micelles to the external leaflets of the liposome bilayers. The modified liposomes are then purified from the mixture by size exclusion chromatography. The range of content of the targeting ligands in the nanocapsules of the invention is in the order of about 0.1-10 mol %. Thus, one may use about 0.1 mol %, 0.2 mol %, 0.5 mol %, 1.0 mol %, 1.5 mol %, 2.0 mol %, 2.5 mol %, 3.0 mol %, 3.5 mol %, 4.0 mol %, 4.5 mol %, 5.0 mol %, 5.5 mol %, 6.0 mol %, 6.5 mol %, 7.0 mol %, 7.5 mol %, 8.0 mol %, 8.5 mol %, 9.0 mol %, 9.5 mol %, or about 10 mol % of the targeting ligand in a nanocapsule. Intermediate ranges such as, about 0.11 mol %, 0.56 mol %, or about 9.9 mol % and the like are also contemplated.

Quantification of the targeting ligand can be done using the following methods:

A. MBP Assay:

MBP-containing liposomes are complexed with $^{99m}$Tc and separated by ultracentrifugation (2×40 min., 30,000 g). The liposomes are then resuspended in scintillation fluid and subjected to liquid scintillation counting. Backgrounds are conducted on non-MBP-containing liposomes subjected to $^{99m}$Tc.

B. Asp$_n$ Assay:

These liposomes are assayed by total nitrogen content. They may also be assayed by $^{14}$C radionucleotide labeling of the Asp$_n$ ligand. Radio labeling can be accomplished by solid state synthesis methods discussed previously (Kasugai el al., 2000; Merrifield, 1963). The Asp$_n$ ligand can also be assayed by ninhydrin-based calorimetric assays.

Example 5

Analysis of Targeting and Adherence Characteristics of Model Protein-Containing Liposomes This analysis can be done using methods similar to those described by Kasugai, et al, 2000. MBP-ligated liposome formulations are be prepared according to prescribed methods. Asp$_6$-ligated liposome formulations are be prepared using $^{14}$C-labeled ligands. Commercial culture plates coated with hydroxyapatite films are be inoculated with formulated liposomes. The plates are be cultured for approximately one-hour at physiologic temperature, after which the liquid is collected from the wells. Wells inoculated with MBP-ligated liposomes are charged with $^{99m}$Tc-spiked buffer to label non-bound MBP. The $^{99m}$Tc-spiked buffer are collected for analysis. The hydroxyapatite films in all wells are digested with 14% EDTA to release attached liposomes. All collected liquids are assayed for radionuclide content by liquid scintillation. The extent of targeting nanocapsule attachment to the hydroxyapatite surface is determined by mass balance. The effect of targeting-ligand concentration on the targeting liposomes can be determined according to experimental plan described in Table 3.

TABLE 3

Nanocapsule Targeting and Adherence Study Plan

| Sample | Ligand Content | Targeting Ligand Type | | Ligand Tether Length | | |
|---|---|---|---|---|---|---|
| | | MBP | Asp$_6$ | Zero | PEG-2000 | PEG-5000 |
| 1 | Low | X | | X | | |
| 2 | | | X | X | | |
| 3 | | X | | | X | |
| 4 | | | X | | X | |
| 5 | | X | | | | X |
| 6 | | | X | | | X |
| 7 | High | X | | X | | |
| 8 | | | X | X | | |
| 9 | | X | | | X | |
| 10 | | | X | | X | |
| 11 | | X | | | | X |
| 12 | | | X | | | X |
| 13 | Zero | | | X | | |
| 14 | | | | | | X |

Example 6

Determination of the Release Kinetics of Payload-Containing Targeting Liposomes In Vitro Nanocapsule stability and the release kinetics of model agents can be determined at physiologic temperature as a function of nanocapsule formulation and time according the design outlined in Table 4. Agent release is determined at 0, ¼, ½, 1, 2, 3, 6, 12, and 24 hours.

TABLE 4

Bilayer Stability and Release Profile Study Plan

| Liposome Type | Targeting Ligand Type | | Ligand Tether Length | | |
|---|---|---|---|---|---|
| | MBP | Asp$_6$ | Zero | PEG-2000 | PEG-5000 |
| 1 | X | | X | | |
| 2 | | X | X | | |
| 3 | X | | | X | |
| 4 | | X | | X | |
| 5 | X | | | | X |
| 6 | | X | | | X |
| 7 | | | X | | |
| 8 | | | | | X |

Liposome membrane integrity is assessed by quantifying the release of 5,6-carboxyfluorscein (CF) according to methods described by Senior et al., (1982) CF is encapsulated in sufficient concentration (>100 mM) to quench its fluorescence and the liposome membrane stability is then determined by quantifying the fluorescence of free CF as it is dequenched by dilution in the incubation medium.

Fluorescein labeled bovine serum albumin is encapsulated according to methods described previously. Protein release is determined by monitoring fluorescence of the incubation medium and corroborated protein content by bicinchoninic acid (BCA) protein assay.

The release profile of BMP-2, a model bone anabolic agent, is determined by an immunoassay (R&D Systems, Inc.). BMP-2 is encapsulated using protocols developed for BSA. BMP-2 is smaller than BSA (26 kDa vs. 66.5 kDa) and has similar solution properties, (Strassman et al., 1991), so its entrapment efficiency should be similar to BSA. All glassware is silanized to prevent protein adhesion. The encapsulation efficiency of strongly charged proteins can be affected by lipid bilayer surface charge and media ionic strength. Small amounts of negatively charged phospholipids (e.g., 0.1-1.0% mol), such as distearoyl-phosphatidylglycerol (DSPG, $T_c$ ~54.2° C.), which have been shown to significantly improve liposome-protein association efficiency, can be included in the liposome formulation (Van Slooten et al., 2001).

Example 7

In Vitro Uptake of Protein-Containing Targeted Liposomes by Isolated Perfused Bone An isolated perfused rabbit tibia preparation is used for analysis of targeted liposomes using a modification of the technique described by Martin et al., (1978). This allows analysis of targeting efficiencies in a system that closely mimics the in vivo environment and the movement of the liposome preparations through intact bone structures and microvasculature.

Large (3 kg) male New Zealand White rabbits are anesthetized using a standard veterinary anesthetic cocktail consisting of ketamine, xylazine and acepromazine administered intramuscularly. The anterolateral aspect of each hind limb is clipped free of hair with a #40 clipper blade and the area prepared for surgery. A longitudinal midline incision is made over the lateral aspect of each hindlimb, the skin retracted and muscle groups exposed. The peroneal muscles are retracted superiorly and the anterior tibial artery exposed to localize the nutrient artery of the tibia. The animals are then heparinized and the tibiae removed. Adhering soft tissues is removed and the nutrient artery cannulated via the main anterior tibial artery. The isolated bones are then perfused at 37° C. with normal saline containing indocyanine green dye (Hynson Westcott and Dunning, Inc., Baltimore, Md., USA) to flush the nutrient-vascular system and establish and verify venous flow from the bone surface and the nutrient vein. Once perfusion is established, the system will be flushed with saline without dye and the experiment begun. A measured quantity of targeted liposomes containing labeled BSA is then added in 5 ml of perfusate, followed by a 5 ml saline flush. Simultaneously with the perfusion of liposome-containing perfusate, venous drainage is collected to a total of 10 ml.

The same plan outlined in Table 3 can be used in this study. Six tibial specimens for each of six study groups may be utilized. Control specimens consist of perfusions of loaded micro-carriers that do not have biolinkage molecules. Study liposomes contain either of two different targeting molecules. The liposomes will typically contain one of two different PEGylated phospholipid conjugates and will contain flurocein-labeled BSA. The collected 10 ml of venous drainage described above will be analyzed for total flurocein-labeled protein content (BSA) using methods previously described. Since the total BSA perfused into each bone will be known, the amount targeted and adherent to bone is calculated as the difference of total in versus total out. The bio-linkage molecule with the greatest targeting efficiency is used as the sole targeting agent in the subsequent in vivo experiments.

Immediately following isolation of the tibiae from each animal, the animals are euthanized. Euthanasia of experimental animals is in full compliance with the recommendations of the American Veterinary Medicine Association (AVMA). Termination is via IV administration of pentobarbital at a dosage rate of 50 mg/kg body weight.

Example 8

Demonstration of In Vitro Nanocapsule Delivery of a Bioactive Factor

Transforming growth factor beta (TGF-β) can be delivered via the targeting nanocapsule carriers of the invention to result in metabolic activation of cell proliferation pathways in osteoblast-like cells in vitro. Transforming growth factor (TGF-β) appears to be a critical factor in tissue and fracture repair and bone formation. TGF-β stimulates the replication of osteoblast precursor cells and has a stimulatory effect on bone-collagen synthesis. TGF-β also induces apoptosis of osteoclast and thus decreases bone resorption. There have been observed decreases in the steady-state levels of TGF-β mRNA in three different models of skeletal underloading, spaceflight, sciatic neurotomy, and hind-limb unloading. Significantly, continuous infusion of TGF-β 2 (2 μg/kg/day) has been shown to prevent the impaired bone formation and osteopenia induced by unloading.

In cell culture systems, TGF-β stimulates increases in DNA synthesis in a dose-dependent manner. DNA synthesis as measured by thymidine incorporation is a sensitive measure of cell proliferation. An effective mechanism to deliver bio-active concentrations of this growth factor to the local bone microenvironment would thus be a desirable goal. To demonstrate that TGF-β encapsulated by the micro-carriers developed in this study is delivered in a bioactive state, MG63 osteoblast-like cells can be exposed to varying concentrations of the factor following release from the carriers. Effects on cell proliferation as measured by thymidine can be then measured.

TGF-β will be encapsulated as described herein for BSA. Western blot analysis can be utilized to characterize the TGF-β released from the liposome preparations (Pedrozo et al., 1998). Liposomes containing TGF-β can be collected into a microcentrifuge tube and digested with 30 μl 0-1.0 U/ml of plasmin for 3 hr at 37° C. Immediately after digestion, each sample may be divided in two equal aliquots and each set run on a 4-20% SDS-polyacrylamide gel. The proteins on the gel are then transferred to nitrocellulose membranes. One membrane can be probed with mouse anti-TGF-β antibody and the other one with mouse IgG as a control. To visualize the bands, the ECL Western blot analysis system can be used according to the manufacturer's instructions.

Study Design

MG63 osteoblast-like cells, originally isolated from a human osteosarcoma, will be obtained from the American Type Culture Collection. This line has been used extensively for studies of osteoblast responses to ceramic matrices and various growth factor effects in culture. Except as noted otherwise, cells will be plated at 9,300 cells/cm² in Dulbecco's modified Eagle medium containing 10% fetal bovine serum and 0.5% antibiotics (diluted from a stock solution containing 5,000 U/ml penicillin and 5,000 U/ml streptomycin). Each culture plate well will contain a total volume of 150 μl. Cells will be cultured in an atmosphere of 100% humidity, 5% $CO_2$ and 37° C. in 24-well culture plates. Media will be changed at 24 hours and then at 72-hour intervals until the cells reach confluence. At confluence, the media will be removed and replaced with media as described in Table 5.

TABLE 5

Cell Culture

| Group | Targeting Ligand Type | | | Ligand Tether Length | |
|---|---|---|---|---|---|
| | TGF-β | MBP | Asp$_6$ | Zero | PEG-2000 |
| Control cells | | | | | |
| Control cells | X | | | | |
| Cells + liposomes | | X | | X | |
| Cells + liposomes | | X | | | X |
| Cells + liposomes | | | X | X | |
| Cells + liposomes | | | X | | X |
| Cells + liposomes | X | X | | X | |
| Cells + liposomes | X | X | | | X |
| Cells + liposomes | X | | X | X | |
| Cells + liposomes | X | | X | | X |

For all cell culture studies, an N of 6 (6 wells) will be obtained for each group and dilution. In study groups containing TGF-β, three dilutions of TGF-β will be utilized such that the maximum dose of TGF-β is 5 ng/ml. Liposome-encapsulated TGF-β will be delivered as follows. Liposome populations containing known amounts of encapsulated TGF-β will be disrupted via sonication. Appropriate aliquots will then be delivered to the culture wells to equal the required TGF-β concentrations. In study liposome groups without TGF-β, equivalent volumes used in groups used to deliver TGF-β will used.

At harvest, cell layers will be prepared and their protein content will be determined using commercial kits. Cell layers will be prepared following standard methods, for example, as described by the method of Hale, et al. At harvest, the culture media will be decanted and the cell layers washed twice with phosphate-buffered saline and then removed with a cell scraper. After centrifugation, the cell-layer pellets will be washed with phosphate-buffered saline and resuspended by vortexing in 500-μl deionized water plus 25-μl 1% Triton X-100.

DNA synthesis in nonquiescent cells will be measured by estimating tritiated thymidine incorporation into trichloro-acetic-acid insoluble cell precipitates. Four hours prior to harvest, 50 μl 3H-thymidine (from a 1 μCi [37,000 Bq]/ml stock solution) will be added to the cultures. At harvest, the cell layers will be washed twice with cold phosphate-buffered saline and twice with 5% trichloroacetic acid and then treated with ice-cold saturated trichloroacetic acid for 30 minutes. Trichloroacetic-acid precipitable material will be dissolved in 0.3ml 1% sodium dodecyl sulfate at 20° C. and radioactivity measured by liquid scintillation spectroscopy.

All data will be expressed as the mean±standard error of the mean (SEM) of six sample cultures or six wells for each study group. Significance between data points and controls will be determined by analysis of variance with statistical significance set at p≦0.05. Experiments will be repeated three times in order to verify consistency of the observations.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 5,013,649
U.S. Pat. No. 5,401,511
U.S. Pat. No. 5,603,872
U.S. Pat. No. 5,648,056
U.S. Pat. No. 5,889,155
PCT/US85/01161
PCT/US89/05040
U.K. Patent GB 2193095A
Allen et al., *Biochim. Biophys. Acta*, 1066:29-36, 1991.
Allen et al., *Biochim. Biophys. Acta*, 1237:99-108, 1995.
Allen, et al., *FEBS Letters*, 460, 129-133, 1999.
Allen, et al., *Pharma. Res.*, 19(3), 265, 2002.
Baldwin et al., *Med. Sci. Sports Exerc.*, 10:1247-1253, 1996.
Bangham, et al., *J Mol. Biol.*, 13:238-252, 1965.
Bikle et al., *J. Bone Miner. Res.*, 9:1777-1787, 1994a.
Bikle et al., *J Bone Miner. Res.*, 9:1789-1796, 1994b.
Carmeliet et al., *Bone*, 22:139S-143S, 1998.
Centrella, et al. *J. Biol. Chem.*, 262:2869-2874, 1987.
Chenu, et al., *Proc. Natl. Acad. Sci. USA*, 85:683-5687, 1988.
Cooper et al., *Quarterly J. Med.*, 87:203-209, 1994.
Cronhjort et al., *Acta Radiol.*, 40:309-311, 1999.
Davis and Jones, *Semin. Nucl. Med.*, 6:19-31, 1976.
Deamer and Uster, In: *Liposomes, Ostro (Ed.), Marcel Dekker, Inc., NY*, 27-52, 1983.
Fleiner et al., *Bioconjugate Chem.*, 12:470-475, 2001.
Forssen and Willis, *Adv. Drug Delivery Reviews*, 29:249-271, 1998.
Fujisaki et al., *J Drug Targeting*, 3:273-282, 1995.
Fujisaki et al., *J Drug. Targeting*, 5:129-138, 1997.
Fujisaki et al., *J. Pharm. Pharmacol.*, 48:798-800, 1996.
Ghosh and Bachhawat, In: *Liver diseases, targeted diagnosis and therapy using specific receptors and ligands*, Wu and Wu (Eds.), NY, Marel Dekker, 87-104, 1991.
Gregoriadis and Davis, *Biochem Biophs Res Commun*, 89:1287-1293, 1979.
Gregoriadis, *DRUG CARRIERS IN BIOLOGY AND MEDICINE*, Gregoriadis (Ed.), 287-341, 1979.
Halloran et al., *J Bone Miner. Res.*, 10:1168-1176, 1995.
Harris et al., *Bone*, 26:325-331, 2000.
Holick, *The Lancet*, 355:1607-1611, 2000.

Jeppesen et al., *Science*, 293:465-468, 2001.
Joseph, *Am. J. Hosp. Pharm.*, 51:188-197,1994.
Kamps et al., *Proc. Natl. Acad. Sci.*, USA, 94:11681-11685, 1997.
Kasugai et al., *J. Bone and Mineral Research*, 15:936-943, 2000.
Kirby and Gregoriadis, In: *Liposome Technology*, Vol. II, CRC Press, Boca Raton, Fla., 1984.
Kirby et al., *FEBS Lett.*, 111:324-328, 1980.
Kontoci et al., *Synth. Comm.*, 26:2037-2043, 1996.
Lantto et al., *Acta Radiol.*, 28:631-633, 1987.
Lasic, In: *Microencapsulation: Methods and Industrial Applications*, Simon Benita (Ed.), Marcel Dekker, NY, 1996.
Lee and Huang, *Biochim. Biophys. Acta*, 1233:134-144, 1995.
Machwate et al., *J. Clin. Invest.*, 96:1245-1253, 1995.
Martin et al., *J. Clin. Invest.*, 261, 256-26, 1978.
Mayer et al., *Biochim Biophys Acta*, 858(1):161-8, 1986.
Mayer et al., *Biochim. Biophys. Acta*, 817:193-196, 1985.
Mayer et al., *Biochim. Biophys. Acta*, 858:161-168, 1986.
Mayhew et al., *Biochim Biophys Acta*, 775(2):169-174, 1984.
McCarthy et al., *Eur. J. Clin. Invest.*, 30:1044-1054, 2000.
Merrifield, *J. Am. Chem. Soc.*, 85:2149-2154, 1963.
Mundy, *Adv. Drug Delivery Rev.*, 42:165-173, 2000.
Mundy, In: *Primer on the metabolic bone diseases and disorders of mineral metabolism*, Favus, (Ed.) Amer. Soc. of Bone and Mineral Research, 16-24, 1996.
Nagata et al., *Biochem. J.*, 274(Pt. 2):513-520, 1991.
National Geographic, January, 2001.
Parfitt et al., *J. Bone Miner. Res.*, 11:150-159, 1996.
Pedrozo et al., *J. Cell. Physiol.*, 177:343-354, 1998.
Remington's Pharmaceutical Sciences, 18th Ed. Mack Printing Company, 1990.
Rho et al., *Medical Engineering and Physics*, 20, 1998.
Senior and Gregoriadis, *Life Sci.*, 30, 2123-2136, 1982.
Strassmann, et al., *Clin. Exp. Immunol.*, 86, 532-536, 1991.
Szoka and Papahadjopoulos, *Proc. Natl. Acad. Sci.*, USA, 75:4194-4198, 1978.
ten Dijke et al., *Bio/Technology*, 7:793-798, 1989.
Thérien and Shahum, *Cell. Immun.*, 116:320-330, 1988.
Trends in Orthopedics, ABM AMRO, Apr. 25, 2000.
Turner, *J. Appl. Physiol.*, 89:840-847, 2000.
Uludag et al., *Biotechnol. Prog.*, 16:1115-1118, 2000a.
Uludag et al., *Biotechnol. Prog.*, 16:258-267, 2000b.
Uster, et al., *FEBS Letters*, 386, 243-246, 1996.
Van Slooten et al., *Biochim. Biophys. Acta*, 1530:134-145, 2001.
Vico et al., *The Lancet*, 355:1607-1611, 2000.
Westerlind and Turner, *J. Bone Miller. Res.*, 10:843-848, 1995.
Wu et al., *Cancer Res.*, 53:3765-3770, 1993.
Yokogawa et al., *Endocrinology*, 142(3):1228-1233, 2000.
Zerath et al., *J. Appl. Physiol.*, 79:1889-1894, 1995.

What is claimed is:

1. A nanocapsule encapsulating at least a first bioactive factor, wherein said nanocapsule is bound to a bisphosphonate targeting ligand having specificity for a component of the systemic skeleton and wherein said nanocapsule is capable of releasing said bioactive factor due to an externally applied signal, a complementary factor administered in schedule or a biochemical signal present in the bone microenvironment, wherein said nanocapsule, when not releasing said bioactive factor, is capable of remaining intact and being expelled by normal metabolic activity, wherein said bisphosphonate targeting ligand prior to binding with the nanocapsule has a structure selected from the following:

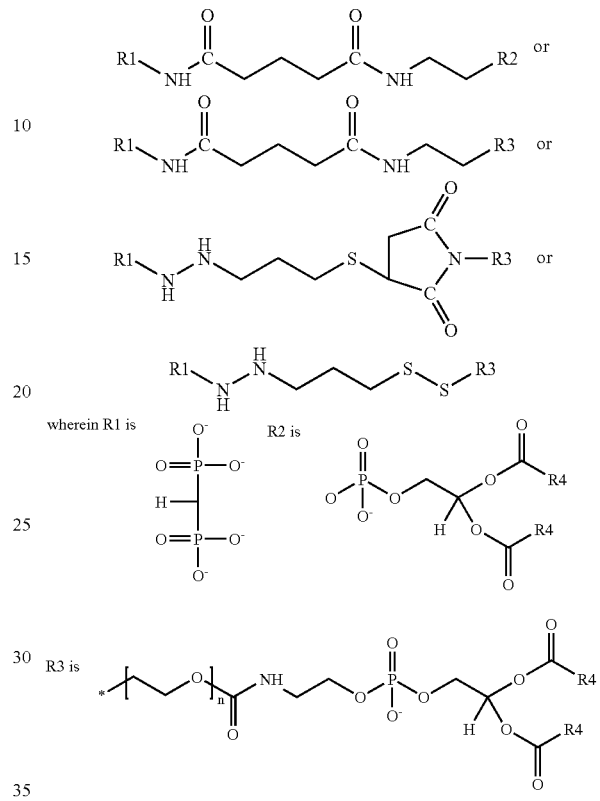

and R4 is an alkyl group.

2. The nanocapsule of claim 1, wherein said ligand is surface bound to said nanocapsule.

3. The nanocapsule of claim 1, wherein said ligand has an affinity for hydroxyapatite in said systemic skeleton.

4. The nanocapsule of claim 1, wherein said nanocapsule has a diameter of from 1 nm to 200 nm.

5. The nanocapsule of claim 4, wherein said nanocapsule has a diameter of about 50 nm.

6. The nanocapsule of claim 4, wherein said nanocapsule has a diameter of about 100 nm.

7. The nanocapsule of claim 4, wherein said nanocapsule has a diameter of about 150 nm.

8. The nanocapsule of claim 4, wherein said nanocapsule has a diameter of about 200 nm.

9. The nanocapsule of claim 1, wherein said bioactive factor is selected from the group consisting of a bone morphogenetic protein, a peptide, estrogen, a bisphosphonate, TGF-β, and an osteotropic agent.

10. The nanocapsule of claim 9, wherein the bioactive factor is an osteotropic agent.

11. The nanocapsule of claim 1, wherein said nanocapsule is a liposome.

12. The nanocapsule of claim 1, wherein said nanocapsule is a niosome.

13. The nanocapsule of claim 11, wherein said liposome is a metalized liposome.

14. The nanocapsule of claim 11, wherein the liposome is unilamellar.

15. The nanocapsule of claim 1, wherein said nanocapsule is a pillared construct.

16. The nanocapsule of claim 1, wherein said nanocapsule is polymer-based.

17. The nanocapsule of claim 1, wherein said nanocapsule is composed of inorganic materials.

18. The nanocapsule of claim 1, wherein said nanocapsule is composed of lipids.

19. The nanocapsule of claim 18, wherein said lipids are phospholipids.

20. The nanocapsule of claim 1, wherein said nanocapsule is a micelle.

21. A method of delivering a bioactive factor to a component of the systemic skeleton of a patient in need thereof comprising:
   (a) obtaining nanocapsules comprising at least a first bioactive factor, wherein said nanocapsules are capable of releasing said bioactive factor due to an externally applied signal, a complimentary factor administered in schedule or a biochemical signal present in the bone environment, wherein said nanocapsule, when not releasing said bioactive factor, is capable of remaining intact and being expelled by normal metabolic activity, wherein said nanocapsule further comprise at least a first bisphosphonate targeting ligand having specificity for a component of the systemic skeleton; and
   (b) administering the nanocapsules to the patient wherein said bisphosphonate targeting ligand prior to binding with the nanocapsule has a structure selected from the following:

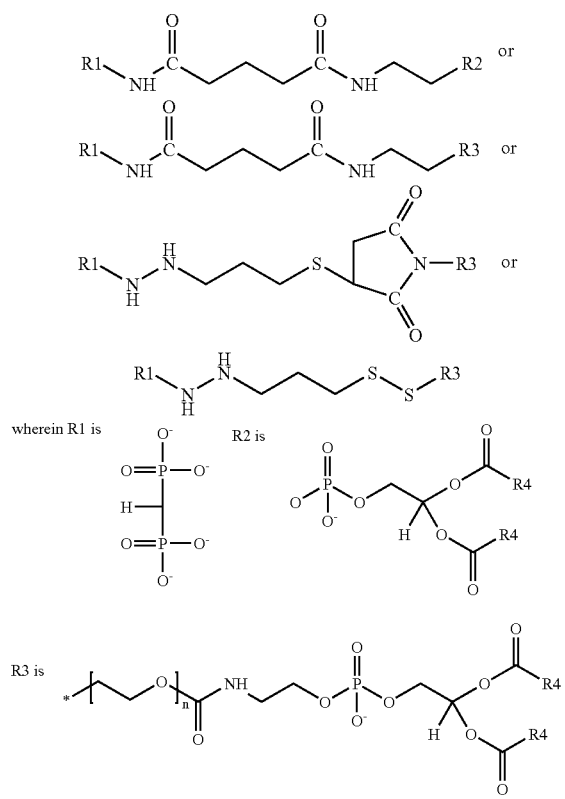

and R4 is an alkyl group.

22. The method of claim 21, wherein said ligand is surface bound to said nanocapsules.

23. The method of claim 21, wherein said ligand has an affinity for hydroxyapatite in said systemic skeleton.

24. The method of claim 21, wherein said nanocapsules are contained in a pharmaceutically acceptable carrier.

25. The method of claim 21, wherein said obtaining is further defined as comprising obtaining a plurality of nanocapsules with different temporal release characteristics.

26. The method of claim 21, wherein said nanocapsules are from 1 nm to 200 nm in diameter.

27. The method of claim 21, wherein said nanocapsules are about 50 nm in diameter.

28. The method of claim 21, wherein said nanocapsules are about 100 nm in diameter.

29. The method of claim 21, wherein said nanocapsules are about 150 nm in diameter.

30. The method of claim 21, wherein said nanocapsules are about 200 nm in diameter.

31. The method of claim 21, wherein said bioactive factor is selected from the group consisting of a bone morphogenetic protein, a peptide, estrogen, a bisphosphonate, TGF-β, and an osteotropic agent.

32. The method of claim 31, wherein said bioactive factor is an osteotropic agent.

33. The method of claim 21, wherein said nanocapsules are liposomes.

34. The method of claim 21, wherein said nanocapsules are niosomes.

35. The method of claim 33, wherein the liposomes are further defined as metalized liposomes.

36. The method of claim 33, wherein the liposomes are unilamellar.

37. The method of claim 21, wherein said nanocapsules comprise a pillared construct.

38. The method of claim 21, wherein said nanocapsules are polymer-based.

39. The method of claim 21, wherein said nanocapsules are composed of inorganic materials.

40. The method of claim 21, wherein said nanocapsules are micellae.

41. The method of claim 21, wherein said nanocapsules are composed of phospholipids.

42. The method of claim 21, wherein said composition is administered locally.

43. The method of claim 21, wherein said composition is administered systemically.

44. The method of claim 21, wherein said composition is administered intravenously.

45. The method of claim 21, wherein said composition is administered intra-arterially.

46. The method of claim 21, wherein said composition is administered topically.

47. The method of claim 21, wherein said composition is administered orally.

48. A method of treating bone loss in a subject in need thereof comprising:
   (a) obtaining nanocapsules comprising at least a first osteotropic factor, wherein said nanocapsules further comprise a first bisphosphonate targeting ligand having specificity for a component of the systemic skeleton wherein said nanocapsules are capable of releasing said bioactive factor due to an externally applied signal, a complimentary factor administered in schedule or a biochemical signal present in the bone environment, wherein said nanocapsule, when not releasing said bioactive factor, is cap able of remaining intact and being expelled by normal metabolic activity; and (b) administering the nanocapsules to the subject wherein said bisphosphonate targeting ligand prior to binding with the nanocapsule has a structure selected from the following:

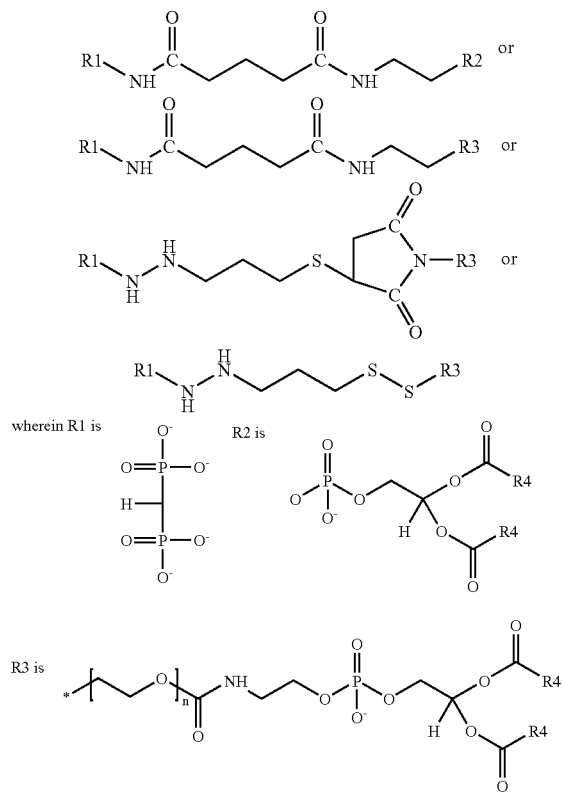

and R4 is an alkyl group.

49. The method of claim 48, wherein said ligand is surface bound to said nanocapsules.

50. The method of claim 48, wherein said ligand has an affinity for hydroxyapatite in said systemic skeleton.

51. The method of claim 48, wherein said osteotropic factor is released from said nanocapsules upon contact of said nanocapsules with a signal released from said systemic skeleton.

52. The method of claim 48, wherein said obtaining is further defined as comprising obtaining a plurality of nanocapsules with different temporal release characteristics.

53. The method of claim 48, wherein said nanocapsules is contained in a pharmaceutically acceptable carrier.

54. The method of claim 48, wherein said nanocapsules are liposomes.

55. The method of claim 48, wherein said nanocapsules are niosomes.

56. The method of claim 54, wherein said liposomes are further defined as metalized liposomes.

57. The method of claim 54, wherein said liposomes are unilamellar.

58. The method of claim 48, wherein said nanocapsules comprise a pillared construct.

59. The method of claim 48, wherein said nanocapsules are polymer-based.

60. The method of claim 48, wherein said nanocapsules are composed of inorganic materials.

61. The method of claim 48, wherein said nanocapsules are composed of lipids.

62. The method of claim 61, wherein said lipids are phospholipids.

63. The method of claim 48, wherein said nanocapsules are micellae.

64. The method of claim 48, wherein said composition is administered locally.

65. The method of claim 48, wherein said composition is administered intranasally.

66. The method of claim 48, wherein said composition is administered systemically.

67. The method of claim 48, wherein said composition is administered intravenously.

68. The method of claim 48, wherein said composition is administered intra-arterially.

69. The method of claim 48, wherein said composition is administered topically.

70. The method of claim 48, wherein said composition is administered orally.

* * * * *